US009445975B2

(12) United States Patent
Anderson

(10) Patent No.: US 9,445,975 B2
(45) Date of Patent: Sep. 20, 2016

(54) COMPOSITION AND METHOD FOR PREPARING STABLE UNILAMELLAR LIPOSOMAL SUSPENSION

(75) Inventor: Penelope M. Anderson, Ada, MI (US)

(73) Assignee: ACCESS BUSINESS GROUP INTERNATIONAL, LLC, Ada, MI (US)

( * ) Notice: Subject to any disclaimer, the term of this patent is extended or adjusted under 35 U.S.C. 154(b) by 825 days.

(21) Appl. No.: 12/245,528

(22) Filed: Oct. 3, 2008

(65) Prior Publication Data

US 2010/0086573 A1    Apr. 8, 2010

(51) Int. Cl.
| | |
|---|---|
| A61K 9/127 | (2006.01) |
| A61K 8/14 | (2006.01) |
| A61K 8/34 | (2006.01) |
| A61K 8/55 | (2006.01) |
| A61K 8/63 | (2006.01) |

(Continued)

(52) U.S. Cl.
CPC ............ *A61K 8/14* (2013.01); *A61K 8/345* (2013.01); *A61K 8/553* (2013.01); *A61K 8/63* (2013.01); *A61K 8/678* (2013.01); *A61K 8/68* (2013.01); *A61K 9/0014* (2013.01); *A61K 9/06* (2013.01); *A61K 9/1271* (2013.01); *A61K 9/1277* (2013.01); *A61Q 19/00* (2013.01); *A61Q 19/08* (2013.01); *B82Y 5/00* (2013.01); *A61K 2800/262* (2013.01); *A61K 2800/413* (2013.01)

(58) Field of Classification Search
CPC .................................................... A61K 9/127
USPC .......................................................... 424/450
See application file for complete search history.

(56) References Cited

U.S. PATENT DOCUMENTS

| | | | |
|---|---|---|---|
| 4,089,801 A | 5/1978 | Schneider | 252/316 |
| 4,288,433 A | 9/1981 | Koulbanis et al. | 424/232 |

(Continued)

FOREIGN PATENT DOCUMENTS

| | | |
|---|---|---|
| CN | 1163563 | 10/1997 |
| EP | 0319638 A1 | 6/1989 |

(Continued)

OTHER PUBLICATIONS

International Search Report and Written Opinion for PCT/US2009/057820, dated Feb. 2, 2011, 14 pages.

(Continued)

*Primary Examiner* — Gollamudi Kishore
(74) *Attorney, Agent, or Firm* — Brinks Gilson & Lione; G. Peter Nichols

(57) ABSTRACT

Compositions and methods for producing and using stable transparent to translucent unilamellar liposomal suspensions are described. The suspensions include a liposome preparation having a uniform plurality of unilamellar liposomal particles with a mean particle size between about 50 nm to about 290 nm. The particles are suspended in an external phase composition that has a density between about 0.95 g/cc and about 1.25 g/cc, and that is present in an amount between about 30% to about 75% of the weight of the liposomal suspension. The liposome preparation is formed from an aqueous liposomal solution that includes an oil-soluble composition and a water-soluble composition. The oil-soluble composition is present at a concentration between about 5% to about 33% by weight of the liposomal solution and the water-soluble composition is present at a concentration between about 67% to about 95% by weight of the liposomal solution.

17 Claims, 10 Drawing Sheets

(51) Int. Cl.
*A61K 8/67* (2006.01)
*A61K 8/68* (2006.01)
*A61K 9/00* (2006.01)
*A61K 9/06* (2006.01)
*A61Q 19/00* (2006.01)
*A61Q 19/08* (2006.01)
*B82Y 5/00* (2011.01)

(56) References Cited

U.S. PATENT DOCUMENTS

| | | | |
|---|---|---|---|
| 4,687,661 A | 8/1987 | Kikuchi et al. | |
| 4,708,816 A | 11/1987 | Chang et al. | 252/186.25 |
| 4,753,750 A | 6/1988 | Ouhadi et al. | 252/139 |
| 4,828,723 A | 5/1989 | Cao et al. | 252/8.8 |
| 4,830,857 A | 5/1989 | Handjani et al. | 424/450 |
| 4,830,858 A * | 5/1989 | Payne et al. | 424/9.33 |
| 4,931,195 A | 6/1990 | Cao et al. | 252/8.8 |
| 5,008,050 A | 4/1991 | Cullis et al. | 264/4.3 |
| 5,021,200 A | 6/1991 | Vanlerberghe et al. | 264/4.3 |
| 5,035,895 A | 7/1991 | Shibusawa et al. | 424/450 |
| 5,041,278 A | 8/1991 | Janoff et al. | 424/1.1 |
| 5,166,139 A | 11/1992 | Bombardelli et al. | 514/26 |
| 5,176,713 A | 1/1993 | Dixit et al. | 8/137 |
| 5,204,105 A | 4/1993 | Mausner | 424/401 |
| 5,234,634 A | 8/1993 | Janoff et al. | 264/4.1 |
| 5,286,629 A | 2/1994 | Denis et al. | 435/7.1 |
| 5,310,556 A | 5/1994 | Ziegler | 424/401 |
| 5,322,839 A | 6/1994 | Voegeli et al. | 514/21 |
| 5,358,752 A | 10/1994 | Evans et al. | 424/450 |
| 5,364,632 A | 11/1994 | Benita et al. | 424/450 |
| 5,368,857 A | 11/1994 | Corcoran et al. | 424/401 |
| 5,378,490 A | 1/1995 | Wheeler et al. | 426/606 |
| 5,380,531 A | 1/1995 | Chakrabarti et al. | 424/450 |
| 5,384,126 A | 1/1995 | Bonte et al. | 424/450 |
| 5,387,579 A | 2/1995 | Meybeck et al. | 514/100 |
| 5,393,530 A | 2/1995 | Schneider et al. | 424/450 |
| 5,411,952 A | 5/1995 | Kaswan | 514/11 |
| 5,429,823 A | 7/1995 | Tremblay et al. | 424/450 |
| 5,470,579 A | 11/1995 | Bonte et al. | 424/450 |
| 5,476,651 A | 12/1995 | Meybeck et al. | 424/59 |
| 5,498,420 A | 3/1996 | Mentrup Edgar et al. | 424/450 |
| 5,523,090 A | 6/1996 | Znaiden et al. | 424/401 |
| 5,534,268 A | 7/1996 | De Paoli et al. | 424/450 |
| 5,560,917 A | 10/1996 | Cohen et al. | 424/401 |
| 5,561,062 A | 10/1996 | Varanelli et al. | 435/238 |
| 5,567,433 A | 10/1996 | Collins | 424/450 |
| 5,593,687 A | 1/1997 | Rossling et al. | 424/450 |
| 5,631,356 A | 5/1997 | Smeets et al. | 536/18.6 |
| 5,637,316 A | 6/1997 | Ribier et al. | 424/450 |
| 5,643,583 A | 7/1997 | Voultoury et al. | 424/401 |
| 5,693,677 A | 12/1997 | Lambers et al. | 514/844 |
| 5,700,482 A | 12/1997 | Frederiksen et al. | 424/450 |
| 5,703,122 A | 12/1997 | Duffy | 514/474 |
| 5,711,965 A | 1/1998 | Ghyczy et al. | 424/450 |
| 5,716,625 A | 2/1998 | Hahn et al. | 424/401 |
| 5,723,059 A | 3/1998 | Snyder, Jr. | 252/70 |
| 5,733,572 A | 3/1998 | Unger et al. | 424/450 |
| 5,736,121 A | 4/1998 | Unger | 424/9.4 |
| 5,741,513 A | 4/1998 | Ghyczy et al. | 424/450 |
| 5,747,006 A | 5/1998 | Dornoff et al. | 424/62 |
| 5,776,488 A | 7/1998 | Mori et al. | 424/450 |
| 5,843,334 A | 12/1998 | Saheki et al. | 252/314 |
| 5,843,474 A | 12/1998 | Williams | 424/450 |
| 5,843,476 A | 12/1998 | Ribier et al. | 424/450 |
| 5,853,755 A | 12/1998 | Foldvari | 424/450 |
| 5,879,703 A | 3/1999 | Fountain | 424/450 |
| 5,888,536 A | 3/1999 | Mezei et al. | |
| 5,895,661 A | 4/1999 | Tournier et al. | 424/450 |
| 5,962,015 A | 10/1999 | Delrieu et al. | 424/450 |
| 5,993,851 A | 11/1999 | Foldvari | 424/450 |
| 6,001,375 A | 12/1999 | Lambers et al. | 424/401 |
| 6,017,558 A | 1/2000 | Bertholet | 424/450 |
| 6,033,708 A | 3/2000 | Kwasiborski et al. | 424/450 |
| 6,034,908 A | 3/2000 | Becker et al. | 365/207 |
| 6,074,647 A | 6/2000 | Zimmerman et al. | 424/195.1 |
| 6,136,330 A | 10/2000 | Soliman et al. | 424/401 |
| 6,183,774 B1 | 2/2001 | Aust et al. | 424/450 |
| 6,184,247 B1 | 2/2001 | Schneider | 514/474 |
| 6,217,899 B1 | 4/2001 | Benameur et al. | 424/450 |
| 6,241,967 B1 | 6/2001 | Sachse et al. | 424/9.321 |
| 6,290,987 B1 | 9/2001 | Modi | 424/450 |
| 6,316,428 B1 | 11/2001 | Crandall | 514/78 |
| 6,350,458 B1 | 2/2002 | Modi | 424/400 |
| 6,350,594 B1 | 2/2002 | Clarke et al. | 435/72 |
| 6,355,267 B1 | 3/2002 | Collins | 424/450 |
| 6,361,806 B1 | 3/2002 | Allen | 424/740 |
| 6,387,373 B1 | 5/2002 | Wright et al. | 424/192.1 |
| 6,399,094 B1 | 6/2002 | Brandl et al. | 424/450 |
| 6,521,237 B2 | 2/2003 | Cole et al. | 424/401 |
| 6,545,052 B2 | 4/2003 | Wohlman et al. | 514/587 |
| 6,576,248 B1 | 6/2003 | Simard et al. | 424/401 |
| 6,586,003 B2 | 7/2003 | Liu et al. | 424/450 |
| 6,630,163 B1 | 10/2003 | Murad | 424/464 |
| 6,753,083 B2 | 6/2004 | Mistry et al. | 428/402 |
| 6,759,073 B2 | 7/2004 | Heisey et al. | 426/573 |
| 6,764,693 B1 | 7/2004 | Smith | 424/450 |
| 6,797,835 B2 | 9/2004 | Fussbroich et al. | 554/80 |
| 6,908,625 B2 * | 6/2005 | Lee et al. | 424/450 |
| 6,926,886 B2 | 8/2005 | Lin et al. | 424/59 |
| 6,960,354 B2 | 11/2005 | Leigh et al. | 424/450 |
| 6,982,284 B1 | 1/2006 | Brown et al. | 514/577 |
| 7,083,572 B2 | 8/2006 | Unger et al. | 600/458 |
| 7,160,560 B2 | 1/2007 | Pinnell | 424/725 |
| 7,169,382 B2 | 1/2007 | Chopart et al. | 424/78.03 |
| 7,179,484 B2 | 2/2007 | Singh | 424/450 |
| 7,182,963 B2 | 2/2007 | Lintner | 424/725 |
| 7,226,583 B2 | 6/2007 | Shepherd, Jr. | 424/62 |
| 7,300,670 B2 | 11/2007 | Venus et al. | 424/489 |
| 7,378,083 B2 | 5/2008 | Stephens et al. | 424/59 |
| 7,384,923 B2 | 6/2008 | Gregoriadis | 514/44 |
| 2002/0035082 A1 | 3/2002 | Grinstaff et al. | 514/44 |
| 2002/0119188 A1 | 8/2002 | Niemiec et al. | 424/450 |
| 2002/0182225 A1 | 12/2002 | Wang et al. | 424/195.11 |
| 2003/0044455 A1 * | 3/2003 | Kazakov et al. | 424/450 |
| 2003/0095959 A1 | 5/2003 | Mayne | |
| 2003/0104046 A1 * | 6/2003 | Patel | 424/450 |
| 2003/0124033 A1 | 7/2003 | Baker et al. | 422/128 |
| 2003/0138481 A1 | 7/2003 | Zadi | 424/450 |
| 2003/0143265 A1 | 7/2003 | Araki et al. | 424/450 |
| 2003/0198610 A1 | 10/2003 | Nakayama et al. | 424/59 |
| 2003/0211126 A1 | 11/2003 | Fitzpatrick et al. | 424/401 |
| 2003/0215414 A1 | 11/2003 | Lambers | 424/70.23 |
| 2003/0224037 A1 | 12/2003 | Eriguchi et al. | 424/450 |
| 2003/0232091 A1 | 12/2003 | Shefer et al. | 424/490 |
| 2004/0062780 A1 | 4/2004 | Keller | 424/401 |
| 2004/0082521 A1 | 4/2004 | Singh | 514/26 |
| 2004/0180082 A1 | 9/2004 | Kang et al. | 424/450 |
| 2004/0224010 A1 | 11/2004 | Hofland et al. | 424/450 |
| 2004/0229794 A1 | 11/2004 | Ryan et al. | 514/12 |
| 2004/0247660 A1 | 12/2004 | Singh | 424/450 |
| 2005/0002999 A1 | 1/2005 | Mehta et al. | 424/450 |
| 2005/0058674 A1 | 3/2005 | Joseph et al. | 424/401 |
| 2005/0058700 A1 | 3/2005 | Wachter et al. | 424/450 |
| 2005/0074468 A1 | 4/2005 | Kim et al. | 424/400 |
| 2005/0095281 A1 * | 5/2005 | Hofland et al. | 424/450 |
| 2005/0107459 A1 | 5/2005 | Franchi et al. | 514/411 |
| 2005/0196416 A1 | 9/2005 | Kipp et al. | 424/400 |
| 2005/0207998 A1 | 9/2005 | Lu et al. | 424/59 |
| 2005/0214357 A1 | 9/2005 | Wang et al. | |
| 2005/0222182 A1 | 10/2005 | Yarkoni et al. | 514/266.22 |
| 2005/0232973 A1 | 10/2005 | Gore | 424/439 |
| 2005/0244488 A1 | 11/2005 | Spilburg | 424/450 |
| 2005/0250756 A1 | 11/2005 | Hofmann | 514/185 |
| 2005/0266065 A1 | 12/2005 | Perrier et al. | 424/450 |
| 2006/0002884 A1 | 1/2006 | Golz-Berner et al. | 424/74 |
| 2006/0008483 A1 * | 1/2006 | Henot et al. | 424/401 |
| 2006/0029657 A1 | 2/2006 | Popp et al. | 424/450 |
| 2006/0034907 A1 | 2/2006 | Nagaike et al. | 424/450 |
| 2006/0034908 A1 | 2/2006 | Bhamidipati et al. | 424/450 |
| 2006/0045896 A1 | 3/2006 | Morariu | 424/401 |
| 2006/0093661 A1 | 5/2006 | Spilburg | 424/450 |
| 2006/0094091 A1 | 5/2006 | Macool et al. | 435/134 |
| 2006/0116404 A1 | 6/2006 | Robinson et al. | 514/359 |
| 2006/0121085 A1 | 6/2006 | Warren et al. | 424/426 |

(56) References Cited

U.S. PATENT DOCUMENTS

| | | |
|---|---|---|
| 2006/0165641 A1 | 7/2006 | Pillai et al. ............... 424/70.22 |
| 2006/0188559 A1 | 8/2006 | Neis et al. .................... 424/450 |
| 2006/0228406 A1 | 10/2006 | Chiou et al. ................ 424/450 |
| 2006/0257386 A1 | 11/2006 | Zimmerman et al. ....... 424/94.6 |
| 2007/0003536 A1 | 1/2007 | Zimmerman et al. ....... 424/94.4 |
| 2007/0003607 A1 | 1/2007 | Awasthi et al. .............. 424/450 |
| 2007/0059746 A1 | 3/2007 | Kuroda et al. .................... 435/6 |
| 2007/0072781 A1 | 3/2007 | Soffin et al. .................. 510/130 |
| 2007/0077292 A1 | 4/2007 | Pinsky ........................... 424/450 |
| 2007/0082042 A1 | 4/2007 | Park et al. ..................... 424/450 |
| 2007/0104774 A1 | 5/2007 | Kim et al. ..................... 424/450 |
| 2007/0110731 A1 | 5/2007 | Riley ........................... 424/93.7 |
| 2007/0148196 A1 | 6/2007 | Haas et al. ..................... 424/401 |
| 2007/0148220 A1 | 6/2007 | Muller et al. ................. 424/450 |
| 2007/0189999 A1 | 8/2007 | Jones et al. ...................... 424/63 |
| 2007/0196914 A1 | 8/2007 | Murray et al. ................ 435/325 |
| 2007/0207110 A1 | 9/2007 | Neis et al. .................. 424/70.13 |
| 2007/0269502 A1 | 11/2007 | Pliura et al. ................... 424/450 |
| 2007/0269566 A1 | 11/2007 | Curtis et al. .................. 426/519 |
| 2008/0045575 A1 | 2/2008 | Van Dyke et al. ............ 514/369 |
| 2008/0081034 A1 | 4/2008 | Zimmerman et al. ....... 424/94.1 |
| 2008/0124409 A1 | 5/2008 | Zimmerman et al. ........ 424/745 |
| 2008/0131497 A1 | 6/2008 | Perkins et al. ................ 424/450 |
| 2008/0138392 A1* | 6/2008 | Leverett et al. .............. 424/450 |
| 2008/0183250 A1 | 7/2008 | Tanojo et al. ..................... 607/88 |
| 2009/0162425 A1* | 6/2009 | Divi et al. ..................... 424/450 |
| 2010/0316696 A1* | 12/2010 | Wiggenhorn et al. ........ 424/450 |

FOREIGN PATENT DOCUMENTS

| | | |
|---|---|---|
| EP | 0707844 A2 | 4/1996 |
| JP | S57-82310 | 5/1982 |
| JP | S60-7932 | 1/1985 |
| JP | S61-502452 | 10/1986 |
| JP | 2002-535268 | 10/2002 |
| JP | 2006-517972 | 8/2006 |
| JP | 2007-277192 | 10/2007 |
| WO | WO 86/00238 | 1/1986 |
| WO | WO 93/20038 | 10/1993 |
| WO | WO 94/26919 | 11/1994 |
| WO | WO 96/12472 | 2/1996 |
| WO | WO 96/37192 | 11/1996 |
| WO | WO 98/33932 | 8/1998 |
| WO | WO 99/65465 | 12/1999 |
| WO | WO 00/42990 | 7/2000 |
| WO | WO 00/47182 | 8/2000 |
| WO | WO 00/69412 | 11/2000 |
| WO | WO 01/41706 A3 | 6/2001 |
| WO | WO 01/42424 A3 | 6/2001 |
| WO | WO 02/05751 A1 | 1/2002 |
| WO | WO 2004/028495 | 4/2004 |
| WO | WO 2004/073684 | 9/2004 |
| WO | WO 2005/044217 | 5/2005 |
| WO | WO 2005/092388 A1 | 6/2005 |
| WO | WO 2006/014035 A1 | 2/2006 |
| WO | WO 2007/064857 A2 | 6/2007 |
| WO | WO 2007/095175 A1 | 8/2007 |
| WO | WO 2007/127439 A2 | 11/2007 |
| WO | WO 2008/043386 | 4/2008 |
| WO | WO 2008/072507 A1 | 6/2008 |

OTHER PUBLICATIONS

Fahr, A, et al., "Skin Penetration Enhancement of Substances by a Novel Type of Liposomes", Cosmetics, SÖFW-Journal, 126. Jahrgang Sep. 2000, (3p).

Fenski, David, et al., "Models of Stratum Corneum Intercellular Membranes: $^2H$ NMR of Macroscopically Oriented Multilayers", Biophysical Journal, vol. 67, Oct. 1994, pp. 1562-1573.

Kirby, Christopher, et al., "Effect of the Cholesterol Content of Small Unilamellar Liposomes on Their Stability in Vivo and in Vitro", Biochem. J. vol. 186, (1980), pp. 591-598.

Koo, S-W., et al., "Protection from Photodamage by Topical Application of Caffeine After Ultraviolet Irradiation", Br. J. Dermatol., 156(5): (2007), pp. 957-964.

Lu, Yao-Ping, et al., "Topical Applications of Caffeine or (—)-Epigallocatechin Gallate (EGCG) Inhibit Carcinogenesis and Selectively Increase Apoptosis in UVB-Induced Skin Tumors in Mice", Proc. Natl. Acad. Sci. USA, 99(19): (2002), pp. 12455-12460.

Madison, Kathi C., "Barrier Function of the Skin: "La Raison d'Etre" of the Epidermis", Epidermal Barrier function, vol. 121, No. 2, Aug. 2003, pp. 231-241.

Mufti, Jabbar, et al., "Skin Care Delivery Systems" Mar. 2001, http://happi.com/special/mar013.html, 9 p.

Thompson, A.K., et al., "Preparation of Liposomes From Milk Fat Globule Membrane Phospholipids Using a Microfluidizer", J. Dairy Sci. 89: (2006), pp. 410-419.

Uhumwangho, Mu, et al., "Current Trends in the Production and Biomedical Applications of Liposomes: A Review", CMS UNIBEN JMBR, 4(1): (2005), pp. 9-21.

Verma, D.D., et al., "Liposomes Increase Skin Penetration of Entrapped and Non-Entrapped Hydrophilic Substances into Human Skin: A Skin Penetration and Confocal Laser Scanning Microscopy Study", European Journal of Pharmaceutics and Biopharmaceutics, vol. 55, (2003), pp. 271-277.

Wen, Ai-Hua, et al., "Formulation of Liposome for Topical Delivery of Arbutin", Arch Pharm Res,vol. 29, No. 12, (2006), pp. 1187-1192.

Search report dated Feb. 4, 2014 in corresponding Chinese Appln. No. 2011-530105 (10 pages including English translation).

* cited by examiner

COMPOSITION AND METHOD FOR PREPARING STABLE UNILAMELLAR LIPOSOMAL SUSPENSION

This invention relates generally to compositions and methods for producing stable, transparent to translucent unilamellar liposomal suspensions with or without loaded active agents for cosmetic, therapeutic, or diagnostic applications.

BACKGROUND

A liposome is a closed generally spherical vesicle with a membrane composed of a phospholipid bilayer that is capable of encapsulating water-soluble, hydrophilic molecules in their aqueous core and embedding oil-soluble, hydrophobic molecules in the hydrophobic region of the bilayer. Liposomes typically are small particles, between about 25 nm to 1000 nm and composed of a variety of phospholipids, including naturally-derived phospholipids with mixed lipid chains, such as egg phosphatidylethanolamine, or of pure components like DOPE (dioleolylphosphatidylethanolamine). Liposomes are widely used in topical drug preparations, by providing a carrier mechanism for deposition of active compounds into the intrinsic layers of the skin. Benefits of employing this technology include controlled release, selective delivery, enhanced bioavailability and stability, and increased absorption of desired actives. In addition, liposomes have a great affinity and compatibility with the skin due to their chemical resemblance to the extracellular lipids surrounding internal skin cells. The lipid bilayer of a liposome can fuse with other bilayers, for example cellular membranes, thus delivering the liposome contents.

The commercial development of liposomes has been plagued by poor stability, clarity, and short shelf life. Liposome vesicles tend to fuse together or agglomerate, particularly when they are exposed to surfactants, solvents, adverse pH conditions, elevated temperatures, or even water, for long periods of time.

SUMMARY

Compositions and methods for producing stable transparent to translucent liposomal suspensions are described herein. The present invention is premised on the discovery that particular combinations of liposomal components can be dispersed in an external phase composition, such that the liposomal suspension retains a unimodal distribution of uniformly sized particles exhibiting stability at various elevated or reduced temperatures with or without active agents for up to a year or more. Specifically, by reducing the mean diameter of the distribution of dispersed liposomal particles, minimizing the density differences between dispersed liposomal particles and the external phase composition, increasing the viscosity of the external phase composition, and building rigidity into the bilayer membrane of vesicles, the stability, clarity and shelf life of the liposomal suspension can be enhanced without sacrificing the structural integrity or bioactivity of the liposomal particles.

In one aspect, a stable unilamellar liposomal suspension includes a liposome preparation suspended in an external phase composition having a density between about 0.95 g/cc and about 1.25 g/cc and a viscosity between about 2.5 cP (centipoise) and about 40,000 cP at a shear rate of 10 sec$^{-1}$ at 21° C. (centigrade). The external phase composition is present in an amount between about 30% to about 75% of the weight of the liposomal suspension. The liposomal suspension has a refractive index between about 1.30 and about 1.45 and is stable with a uniform distribution of particles in neat form at a temperature of between about 4° C. to about 50° C. for a period of at least 30 days, or at 21° C. for a period of at least 180 days, or both. The liposomal suspension includes a plurality of unilamellar liposomal particles having a mean particle size between about 50 nm to about 290 nm. The liposome preparation is formed from an aqueous liposomal solution that includes an oil-soluble composition and a water-soluble composition. The oil-soluble composition is present at a concentration between about 5% to about 33% by weight of the liposomal solution, the water-soluble composition at a concentration between about 67% to about 95% by weight of the liposomal solution. The oil-soluble composition includes a coupling agent, at least one phospholipid, at least one rigidity enhancer, and an antioxidant.

In another embodiment, the liposome preparation is formed using an oil-soluble composition that includes one or more of a lecithin preparation, butylene glycol, ceramide IIIB, β-sitosterol, and tocopherol. In this embodiment, the liposomal suspension includes glycerin at a concentration between about 35% to about 75% of the liposomal suspension.

In another aspect, a method for making a stable unilamellar liposomal suspension includes: (a) preparing an oil-soluble composition comprising a coupling agent, at least one phospholipid, a rigidity enhancer, and an antioxidant; (b) preparing a water-soluble composition; (c) combining the water-soluble composition with the oil-soluble composition to form a multilamellar, multivesicular liposome preparation; (d) converting the multilamellar, multivesicular liposome preparation to a unilamellar liposome preparation; and (e) adding the unilamellar liposome preparation to an external phase composition having a density within a range of about 0.95 g/cc to about 1.25 g/cc and a viscosity between about 2.5 cP and about 40,000 cP at a shear rate of 10 sec$^{-1}$ at 21° C. to form the liposomal suspension comprising a plurality of unilamellar liposomal particles each having a mean particle size between about 50 nm to about 290 nm, wherein the liposomal suspension has a refractive index between 1.30 and 1.45 and retains its stability with a uniform distribution of particles in neat form at about 4° C. to about 50° C. for a period of at least 30 days, or at 21° C. for a period of at least 180 days, or both.

In a further aspect, a method for preparing a cosmetic formulation includes combining a liposomal suspension of the present invention with a cosmetically suitable matrix to form a cosmetic formulation in the form of a cream, lotion, gel, serum, tonic, emulsion, paste, or spray.

The liposomal suspensions of the present invention are characterized by an enhanced stability and biological activity profile and may be useful in any one of a variety of cosmetic, therapeutic, or diagnostic applications where liposomes are used. In addition, the translucent nature of the disclosed liposomal suspensions provides an aesthetically advantageous appearance over more opaque formulations used in the prior art.

DETAILED DESCRIPTION

Figure 1A:
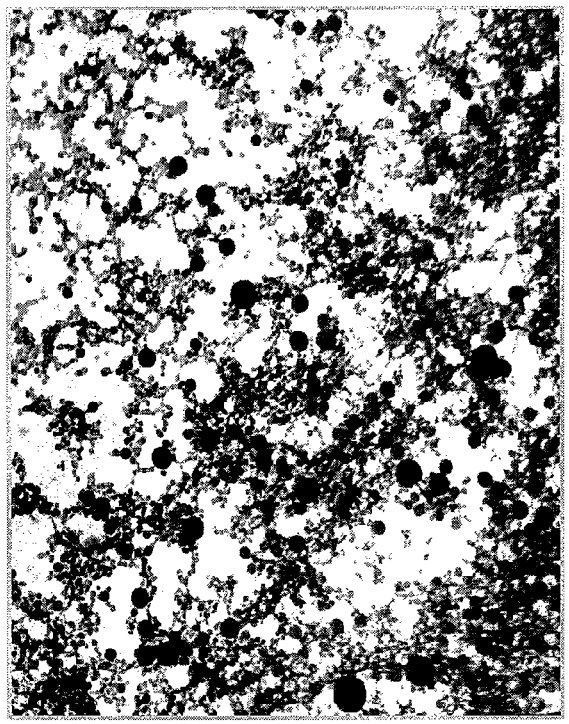
FIG. 1A is an electron micrograph of a liposomal suspension according to an embodiment of Table 2 taken using a Zeiss-902 transmission electron microscope (TEM) at 30,000× magnification.

In order to provide a clear and consistent understanding of the specification and claims, the following definitions are provided.

The term "liposomal solution" refers to a preparation of liposomal particles or vesicles in a concentrated, aqueous solution prior to suspension in an external phase composition.

The term "liposome preparation" refers to a preparation of liposomal particles or vesicles. The liposome preparation may be a liposomal solution containing liposomal particles in an aqueous solution (for example, prior to suspension in an external phase composition) or it may be a preparation of lyophilized (freeze-dried) liposomal particles or vesicles prepared from a liposomal solution.

The term "liposomal solution" refers to a liposome preparation comprising liposomal particles or vesicles in an aqueous solution prior to lyophilization or suspension in an external phase composition.

The term "liposomal suspension" refers to a liposome preparation suspended in an external phase composition.

The term "coupling agent" refers to a connective medium suitable for solubilizing immiscible phases of differing polarity and for effectuating and preserving stability of the liposome preparation or liposomal suspension.

The term "rigidity enhancer" refers to a sphingolipid, ceramide, or sterol functioning to reduce the movement or fluidity of fatty acid chains when embedded in a lipid bilayer and promoting the packing thereof.

Unless indicated otherwise, all proportions and percentages cited in this disclosure are by weight. Further, the contents of all references, patents, and published applications cited throughout this patent are hereby incorporated by reference herein.

In one aspect, the present invention provides a stable translucent unilamellar liposomal suspension that includes a liposome preparation, which comprises a plurality of unilamellar liposomal particles having a mean particle size between about 50 to about 290 nm, where the liposome preparation is suspended in an external phase composition comprising between about 30% to about 75% of the weight of the liposomal suspension. The external phase composition has a density between about 0.95 g/cc and about 1.25 g/cc and a viscosity between about 2.5 cP and about 40,000 cP at a shear rate of 10 sec$^{-1}$ at 21° C. The liposomal suspension has a refractive index between about 1.30 and about 1.45 and is stable in neat form at a temperature of between about 4° C. to about 50° C. for a period of at least 30 days, or at 21° C. for a period of at least 180 days, or both.

Liposome Preparations and Suspensions

A liposome preparation includes a plurality of liposomal particles or vesicles in an aqueous liposomal solution or a plurality of lyophilized (freeze-dried) liposomal particles originating from the liposomal solution. The liposomal particles or vesicles in the liposome preparation may be in a multilamellar, multivesicular form or they may be in a substantially unilamellar form. A liposome preparation is added to the external phase composition to form a liposomal suspension in accordance with the present invention as further described below. The liposomal particles in the liposome preparation are formed from an aqueous liposomal solution comprised of an oil-soluble composition and a water-soluble composition.

Oil-Soluble Composition

The oil-soluble composition includes a coupling agent, a phospholipid or phospholipid mixture, a rigidity enhancer, and an antioxidant. The oil-soluble composition in the liposomal suspension of the present invention will generally comprise a plurality of lipids normally present in native cellular membranes, including phospholipids, ceramides, sphingolipids, cholesterol, and triglycerides, or other lipids such as phytosterols from plants. The oil-soluble composition is present at a concentration between about 5% to about 33% by weight of the aqueous liposomal solution and the water-soluble composition is present in a concentration between about 67% to about 95% by weight of the aqueous liposomal solution.

Coupling Agents

The oil-soluble composition in the liposomal suspension of the present invention will include at least one coupling agent. A coupling agent includes a connective medium suitable for solubilizing (for example, transiently or preferentially) immiscible phases of differing polarity suitable for solubilizing immiscible phases of differing polarity and for maintaining stability of the liposome preparation or liposomal suspension. The coupling agent may be characterized by a dielectric constant of about 10.5 or greater at 23° C., which is added to the liposomal preparations or suspensions of the present invention to facilitate preferential or "transient" solubilization and to effectuate and preserve liposomal stability. A coupling agent, such as a glycol, for example, may include both hydrocarbon and hydroxyl moieties which can be utilized, for example, to simultaneously solubilize hydrophobic or hydrophilic compounds, respectively.

The coupling agent allows for preferential solubilization of oil-phase components, including phospholipids and rigidity enhancers at higher temperatures, whereby the coupling agent migrates into the bilayer membrane components during formation of the liposomal structures in the liposomal solution and then, upon cooling, migrates back into the water-phase due to its hydrophilic properties under ambient temperature conditions. Thus, the coupling agent may be characterized as a "transient solubilizer" capable of solubilizing oil-soluble components, including lipids and nonpolar substances, at high temperatures, and water-soluble components, including polar substances at lower, ambient temperatures (and an inability or reduced ability to solubilize lipids under these low temperature conditions). Accordingly, the coupling agent has a "changing" or transient functionality that is temperature dependent so as to facilitate bilayer membrane formation, including temperature phase combinations producing liquidified forms of cursory multilamellar, multivesicular liposomal structures that can be effectively processed into unilamellar structures under high shear conditions. The lower temperatures avoid compromising the biological activity of active substances and reduce the effects of overheating associated with, for example, high shear/high pressure equipment.

In contrast to coupling agents, other oil-soluble solubilizers that can dissolve bilipid membranes, such as ethanol, may compromise liposomal stability and can present an explosion hazard when processing a liposomal solution through high pressure devices, including microfluidic devices. Moreover, at concentrations above about 3%, ethanol can disrupt the density balance of the colloidal system and reduce the viscosity of the external phase so as to negatively impact upon colloidal stability and/or cause the collapse of gellant structures.

Applicants have unexpectedly discovered that incorporation of a coupling agent not only serves to facilitate solubilization of oil-soluble components, but functions as a stability enhancer, independent of whether oil-soluble actives are included. In particular, Applicants have found that liposomal suspensions lacking a coupling agent, but otherwise identical in composition, did not achieve suitable stability. As such, Applicants believe that the use of coupling agents in the liposomal suspensions of the present invention does not constitute an art-recognized, result-effective variable with respect to stability. Suitable coupling agents include butylene glycol, propylene glycol, hexylene glycol, polyethylene glycols, silicone glycols, such as PEG-12 dimethicone, as well as analogs, derivatives, and mixtures thereof. The coupling agents for use in the present invention may be present in a collective amount ranging from about 1% to about 10% by weight of the liposomal suspension, more desirably from about 3% to about 8% by weight of the liposomal suspension. Generally, the concentration of coupling agent(s) should equal or exceed the total concentration of phospholipids in the liposomal solution. The use of coupling agent concentrations between 10-15% may allow for slightly greater solubilization of active ingredients, particularly when using higher phospholipid concentrations (e.g., 1.5×). However, it is believed that coupling agent concentrations above 10% may cause a phase inversion where the oil-phase exists in an external continuum, thereby preventing liposomal microencapsulation. Under these conditions, water is repelled from the lipid solution in a manner consistent with water-in-oil emulsions. This can be observed visually under a microscope or it can deduced by an inability to accurately measure pH due to hydronium ion shielding. Alternatively, coupling agents may be used at concentrations exceeding the phospholipid concentration where there is a need to solubilize not only the oil phase components, but actives in the water-soluble composition as well.

Phospholipids

The oil-soluble composition in the liposomal suspension of the present invention includes at least one phospholipid or phospholipid mixture. Exemplary phospholipids include, glycerophospholipids comprising saturated and/or unsaturated fatty acyl moieties, including phosphatidylcholine, phosphatidylethanolamine, phosphatidylinositol, phosphatidic acid, N-acylphosphatidylethanolamine, lysophospholipids, and cardiolipins; sphingomyelin; plasmalogens; hydrogenated, partially hydrogenated, or unhydrogenated derivatives thereof; analogs thereof; and mixtures thereof.

Lysophospholipids are obtained when an acyl radical is cleaved off by a phospholipase A from phospholipids (e.g. lysolecithins). Cardiolipins, such as 1,3-bisphosphatidyl glycerol, are phospholipids comprised of two phosphatidic acids linked via glycerol. Sphingomyelins are a type of sphingolipid typically comprised of a phosphorylcholine and a ceramide. Plasmalogens are ether lipids having in which the first carbon position of glycerol has an ether-linked alkene, the second carbon has a typical ester-linked fatty acid, the third carbon typically having a phospholipid head group like choline or ethanolamine.

Exemplary phospholipid mixtures include lecithins, including crude lecithins, which have been deoiled, fractionated, spray-dried, acetylated, hydrolyzed, hydroxylated, hydrogenated, and/or enriched with phosphatidylcholine, phosphatidylinositol, or combinations thereof. Lecithins and lecithin mixtures available commercially. In some embodiments, natural sources of lecithin (soy/egg) may be used, such as phosphatidylcholine-enriched preparations derived from soy.

Commercially available soy/egg lecithin preparations and phospholipid concentrates, include those sold under the trade names Phospholipon® 90G, Phospholipon® 90H, Phospholipon® 85G, Phospholipon® 80H, Phospholipon® 80, Phosal® 50 PG, Phosal® 50 SA, Phosal® 53 MCT, and Phosal® 75SA, which are available from American Lecithin Company, Oxford Conn.; Lipoid® S75, Lipoid® S100, Lipoid® SPC, and Lipoid® SL80, which are available from Lipoid GmbH, Ludwigshafen Germany; Epikurone 125F, Epikuron® 135F, Epikurone 130P, Epikuron® 130G, Epikuron® 100H, Epikuron® 145V, Epikuron® 170, Epikuron® 200 SH, Epikuron® 200, Emulmetik® 950, Emulmetik® 900 and Emulmetik® 300, Emulfluide F30 (Emulfluid, Lipotin Nebr.), Lipotin® 100, Lipotin® SB, Lipotine 100J, Lipotin® H, Lipotin® NA, Lipotin® AH, and Lipopur®, which are available from Degussa Texturant Systems UK Ltd.; Terradrille® V 408 and Terradrill® V 1075, which are commercially available from Cognis; Yellowthin® 100, Yellowthin® 200, Lecistar Sun® 100, and Yellowthin Sun® 200, which are available from Sternchemie; Lecinol S-10 (hydrogenated lecithin), which is available from Barnett Industries; Lipo H (hydrogenated soybean lecithin comprised of 20% phosphatidylcholine), which is available from Lucas Meyer Cosmetics, South Plainfield, N.J.; and Lanchem® PE-130K, which is available from Lambent Technologies, Gurnee, Ill.

The phospholipids for use in the present invention may be present in a collective amount ranging from about 1% to about 10% by weight of the aqueous liposomal solution prior to lyophilization or addition to the external phase composition, more desirably from about 3% to about 8% by weight of the liposomal solution. In addition, the aqueous liposomal solution will desirably contain a water to lipid ratio between about 3:1 to 9:1.

In one embodiment, the oil-soluble composition includes a phospholipid preparation or mixture comprising at least 60% phosphatidylcholine by weight of the mixture, at least 70% by weight, at least 80% by weight, at least 85% by weight, or at least 90% by weight of the mixture. In another embodiment, the oil-soluble composition includes a phospholipid mixture comprising phosphatidylcholine at a concentration between about 80% to about 95% by weight of the phospholipid mixture. Additionally, the above described phospholipid mixtures may comprise between about 1% to about 10% by weight of the liposomal suspension, desirably between about 3% to about 8% by weight of the liposomal suspension. It is believed that the use of phospholipid concentrations above 15% will cause phase inversion resulting in water-in-oil emulsions instead of encapsulated liposomes.

Rigidity Enhancers

The oil-soluble composition in the liposomal suspension of the present invention will include at least one rigidity enhancer. Rigidity enhancer(s) include at least one sphingolipid, ceramide, sterol, or combination thereof, which function to reduce the movement or fluidity of fatty acid chains when embedded in a lipid bilayer and to promote packing of the lipid bilayers. The increased rigidity can reduce rupture and leakage of vesicles and can shift the zeta potential or charge in the membrances so as to suppress attraction between particles. It is believed that the rigidity enhancer(s) help to stabilize the charge or zeta potential in the liposomal particles.

Sphingolipids represent key epidermal lipids involved in maintaining the skin's barrier function. Sphingolipids, such as sphingosine, sphinganine, sphingomyelin, and phytosphingosine, generally comprise a long sphingoid base as the central group or "backbone", including an amide-linked long-chain fatty acid and a head group. There are hundreds of known classes of sphingolipids with different head groups (e.g. cholinephosphate, glucose, galactose, polysaccharides) and with different fatty acids and sphingoid bases. Phytosphingosine is a ceramide precursor, concentrated in healthy stratum corneum that is converted to sphingolipids by enzymes in the skin.

Ceramides constitute a family of sphingolipids, which are extremely insoluble and difficult to formulate. Exogenously administered ceramides must be able to penetrate the stratum corneum in order to reach the lipid lamellae of the permeability barrier. It is believed that one of the causes of dry skin is a reduction in the amount of ceramides within the intercellular lipid lamellae. It is therefore desirable to be able successfully to replace these depleted lipids by topical administration using liposomal suspensions of the present invention. The liposomal suspensions of the present invention provide a useful means for delivery of ceramides.

The ceramide may be a naturally-occurring ceramide, synthetic ceramide, glycosylceramide, or derivatives therefrom. Naturally-occurring ceramides may be derived from animals, plants, or microorganisms. Ceramides in skin are primarily composed of 6 chromatographically distinct fractions or families categorized as types I, II, III, IV, V, VIa, and VIb (or 1, 2, 3, 4, 5, 6a, and 6b). Synthetic (or hybrid) ceramides are ceramide-like sphingolipids, wherein the N-acyl group is other than those found in naturally-occurring ceramides. Ceramides may be differentiated from one another, for example, by degree of saturation and chain length. Ceramide derivatives include, for example, those derivatized with one or more saturated or unsaturated fatty acids, or those modified by phosphorylation or sulfation.

Type 3 ceramides constitute a mixture of different molecules having a phytosphingosine backbone that are characterized by the general name N-acylphytosphingosine, wherein the acyl group is saturated and has a chain length of 14 to 30 carbons. In one embodiment, the ceramide may be a ceramide or phytosphingosphine derivatized with a mono-unsaturated fatty acid, such as N-oleoylphytosphingosine (ceramide 3B). Additional ceramides are disclosed in U.S. Pat. Nos. 5,693,677 and 6,001,375 to Lambers et al., the disclosures of which are incorporated by reference herein.

Ceramides for use in the present invention may be present in a collective amount ranging from about 0.01% to about 1.00% by weight of the liposomal suspension, more desirably from about 0.025% to about 0.20% by weight of the liposomal suspension.

Sterols for use in the present invention represent an additional class of rigidity enhancers, which includes cholesterols, phytosterols, and organic acid derivatives, and/or salt forms thereof. Phytosterols are plant-derived lipids bearing a sterol skeleton. Phytosterols can synchronize metabolic cycles of epidermal cells in skin and can enhance the strength of a septum having a bilayer membrane structure in a liposome or other membranous structure.

The present invention may utilize a member of any of the phytosterol categories, including the 4-desmethylsterols, 4-monomethylsterols, and 4,4-dimethylsterols. Exemplary phytosterols include sitosterol, beta-sitosterol, stigmasterol, campesterol, chalinosterol, clionasterol, brassicasterol, alpha-spinasterol, Δ5-avennasterol, lupenol, dancosterol, desmosterol, and poriferasterol.

Non-limiting examples of sterols additionally include cholesterol, organic acid derivatized cholesterols, such as cholesterol hemisuccinate, phytocholesterol, bisabolol, steroid hormones, such as hydrocortisone, as well as sterol aliphatic acid esters, such as cholesterol sulfate, cholesterol butyrate, cholesterol isobutyrate, cholesterol palmitate, cholesterol stearate, lanosterol acetate, ergosterol palmitate, and phytosterol n-butyrate; and sterol esters of sugar esters, such as cholesterol glucuronide, lanosterol glucuronide, 7-dehydrocholesterol glucuronide, ergosterol glucuronide, and cholesterol gluconate.

Sterols for use in the present invention may be present in a collective amount ranging from about 0.01% to about 1.00% by weight of the liposomal suspension, more desirably from about 0.025% to about 0.20% by weight of the liposomal suspension.

In one embodiment, the liposomal suspension includes at least two rigidity enhancers, including at least one phytosterol and either a ceramide or a sphingosine. In a desired embodiment, the liposomal suspension includes ceramide IIIB and β-sitosterol.

The rigidity enhancers for use in the present invention may be present in a collective amount ranging from about 0.02% to about 1.00% by weight of the liposomal suspension, more desirably from about 0.05% to about 0.40% by weight of the liposomal suspension.

Applicants have unexpectedly discovered a relationship between the use of rigidity enhancers and liposomal stability. More particularly, Applicants have discovered that the stability of liposomes depend on the incorporation of rigidity enhancers over a relatively narrow concentration range. Specifically, incorporation of rigidity enhancers at levels exceeding 1.0% or exceeding a 1:4 ratio by weight relative to the phospholipids, was found to shift the morphology of the microstructure to lamellar sheets, in contrast to spherical liposomal vesicles. For example, 100-400× magnification microscopy has confirmed the creation of lamellar sheets when using rigidity enhancers at greater than 25% of the phospholipid levels, which were further converted to large needle structures upon aging that were detectable to the naked eye.

Antioxidants

According to the present invention, at least one antioxidant is embedded in a liposome. The antioxidant may, for example, be embedded in the phospholipid bilayer of the liposome, in the aqueous center of the liposome, or both. The antioxidant(s) may function to protect the liposome from oxidative damage or degradation resulting either from the aqueous center of the liposome or from reactive oxygen species (ROS) outside the liposome. Indeed, one major action of antioxidants in cells is to prevent damage due to the action of ROS. Reactive oxygen species include hydrogen peroxide ($H_2O_2$), the superoxide anion ($O_2^-$), and free radicals such as the hydroxyl radical ($OH^-$). These molecules are unstable and highly reactive, and can damage cells by chemical chain reactions such as lipid peroxidation.

Antioxidants may be incorporated into liposomes of the present invention in a number of different ways. In one example, a lipid soluble antioxidant may be directly embedded into the lipid bilayer of the liposome. In another example, a water-soluble antioxidant may be encapsulated in the aqueous center of the liposome. In a further example, a lipid soluble antioxidant may be embedded in the lipid bilayer and a water-soluble antioxidant is encapsulated in the aqueous center of the lipid bilayer.

In another example, the antioxidant may be a singlet-oxygen scavenger. In another example, the antioxidant may be both water-soluble and a singlet-oxygen scavenger or both lipid soluble and a singlet-oxygen scavenger. In a further example, more than one antioxidant might be embedded in the liposome of the present invention.

Tocopherol (i.e. vitamin E) and ascorbic acid (i.e. vitamin C) are examples of antioxidants that may be embedded in the liposomes of the present invention. Suitable tocopherol antioxidants include tocopherol; monomethyl, dimethyl, or triethyl derivatives of tocol, including but not limited to, alpha tocopherol, beta tocopherol, gamma tocopherol, delta tocopherol, epsilon tocopherol, zeta tocopherol, and eta tocopherol; tocopherol esters, and derivatives therefrom, including tocopheryl acetate, tocopheryl succinate, tocopheryl benzoate, tocopheryl propionate, tocopheryl sorbate, tocopheryl oleate, tocopheryl orotate, tocopheryl linoleate, tocopheryl nicotinate, and the 2-ethyl-hexanoate ester.

In addition to its antioxidant function, ascorbic acid (Vitamin C) and its derivatives are additionally known to promote collagen synthesis. Ascorbic acid derivatives useful in the present invention include all enantiomers whether singly or in combination. Desirably, the ascorbic acid is provided in the levo form. In addition, the ascorbic acid or its derivatives may be in a water-soluble or an oil-soluble form.

Non-exclusive examples of vitamin C (ascorbic acid) derivatives include, for example, alkyl esters of L-ascorbic acid where the alkyl portion has from 8 to 20 carbon atoms. With respect to the esters, they may be selected from the group consisting of fatty acid mono-, di-, tri- or tetra-esters of ascorbic acid. For example, such esters include, but are not limited to ascorbyl palmitate, ascorbyl laureate, ascorbyl myristate, ascorbyl stearate, ascorbyl dipalmitate, ascorbyl dilaurate, ascorbyl dimyristate, ascorbyl distearate, ascorbyl tripalmitate, ascorbyl trilaurate, ascorbyl trimyristate, ascorbyl tristearate, tetrahexyldecyl ascorbate, ascorbyl tetralaurate, ascorbyl tetramyristate, ascorbyl tetrastearateL, L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate, tetrahexyldecyl ascorbate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; their salts with alkaline earth metals such as calcium and magnesium.

With respect to the salts, they may be selected from the phosphates and sulfates, desirably phosphate. The ascorbic acid phosphate is generally selected from L-ascorbic acid 3-phosphate, L-ascorbic acid 2-phosphate, L-ascorbic acid 3-pyrophosphate and bis(L-ascorbic acid 3,3-) phosphate. Desirably, the ascorbic acid phosphate is magnesium or sodium ascorbyl phosphate; more desirably, magnesium ascorbyl phosphate. Likewise, the ascorbic acid sulfate is generally selected from L-ascorbic acid 3-sulfate, L-ascorbic acid 2-sulfate, L-ascorbic acid 3-pyrosulfate and bis (L-ascorbic acid 3,3-) sulfate.

Additional antioxidants include tetrahexyldecyl ascorbate, butylated hydroxytoluene (BHT), butylated hydroxyanisole, methylgentisate, L-carnosine, tert-butylhydroquinone (TBHQ), glutathione, including derivatives, combinations, and mixtures thereof. In one example, water-soluble L-carnosine may be incorporated into the aqueous center of the liposome for use as an antioxidant, in view of its ability to protect the liposome from oxidative damage via its aqueous center.

Antioxidants for use in the present invention may be present in a collective amount ranging from about 0.01% to about 1.00% by weight of the liposomal suspension, more desirably from about 0.025% to about 0.50% by weight of the liposomal suspension.

Water-Soluble Composition

The water-soluble composition will be primarily comprised of water with or without loaded active (water-soluble) agents, which are further described below. Generally, the water-soluble composition will range from about 10% to about 65% by weight of the liposomal suspension or from about 67% to about 95% by weight of the liposome preparation.

External Phase Composition

The liposomal particles in the liposomal suspension are surrounded by an external composition comprising an aqueous solution including one or more viscosity promoting agents collectively sufficient for the external phase composition to have a density between about 0.95 g/cc to about 1.25 g/cc and/or a viscosity generally between about 2.5 cP and about 40,000 cP at a shear rate of 10 $sec^{-1}$ at 21° C. The one or more viscosity promoting agents may include one or more thickening agents, gellant agents, or both. In a desired embodiment the external phase composition has a viscosity between about 800 cP and 20,000 cP at a shear rate of 10 $sec^{-1}$ at 21° C. Alternatively, when using higher gellant concentrations, the external phase viscosity may be raised to about 60,000 to 80,000 cP at a shear rate of 10 $sec^{-1}$ at 21° C., albeit with reduced clarity.

The external phase composition generally comprises a density closely matching that of the liposomal particles dispersed therein and is incorporated into the liposomal suspension of the present invention in an amount sufficient to promote liposomal particle stability and reduce liposomal particle migration, flocculation, or agglomeration.

The external phase composition includes one or more viscosity promoting agents, including thickening agents, densification agents, gellants, gums, and other viscosity promoting agents known to those of skill in the art. Viscosity promoting agents for use in the present invention may be empirically selected to increase viscosity and enhance stability of the liposomal formulations herein. Desirably, these agents are chosen to preserve the translucent or transparent nature of the liposomal suspension. Further, the compositions may be adjusted by using agents selected to provide a comparatively greater impact on viscosity or density as desired. Exemplary viscosity promoting agents include glycerin; celluloses, including hydroxyethyl-hydroxypropyl-, hydroxymethyl-, hydroxypropylmethyl celluloses, and their derivatives, including various celluloses those under the tradenames Natrosol®, Methocel®, and Bermocoll®; light non-ionic emulsions; and polysorbates. Exemplary gellants and/or thickening agents include gum matrix agents, including xanthan gum, and acrylate polymers, including high molecular weight homo- and copolymers of acrylic acid crosslinked with polyalkenyl polyethers or divinyl glycol under the tradename Carbopol®, including Carbopol® 934, 940, 941, 980, 981, 1342, 1382, 2020, 2050, and various hydroxyethyl acrylate/acryloyidimethyltaurate copolymers under the tradename Simulgel®.

The external phase composition may have Newtonian or non-Newtonian flow characteristics. In one embodiment, the one or more viscosity promoting agents includes an aqueous solution having Newtonian flow characteristics, such as glycerin. The viscosity of Newtonian fluids, including glycerol, is independent of shear rates at given rotation speeds imparted to the fluid. External phase compositions comprising Newtonian flow characteristics may have a viscosity between about 500 cP to about 10,000 cP, or between about 800 cP to about 2,000 cP.

In another embodiment, the one or more viscosity promoting agents may include one or more agents at concentrations between about 0.10% to about 1.0%, such as polymeric gellant agents, which confer non-Newtonian flow characteristics. Non-Newtonian fluids including, for example, polymeric gellants or thickeners, exhibit reduced viscosity as a function of shear rate. However, compared to Newtonian fluids such as glycerin, polymeric gellants can confer non-Newtonian flow characteristics at low concentrations and can provide an apparent viscosity that is comparatively less affected by temperature.

The viscosity of non-Newtonian fluids may be classified in terms of shear and time dependency. Thus, a non-Newtonian fluid may be shear-thinning and shear-thickening. Further, a reduction in apparent viscosity may be time-independent (pseudoplastic) or time-dependent (thixotropic). In a desired non-Newtonian embodiment, the fluid has pseudoplastic shear-thinning properties characteristic of Carbopol® polymers.

At a relatively low shear rate of 10 sec$^{-1}$, the viscosity of an external phase composition containing gellants or thickeners conferring non-Newtonian flow characteristics may vary between about 500 cP to about 80,000 cP at 21° C., between about 800 cP and 40,000 cP, or between about 2,000 cP and 20,000 cP. In one embodiment, when using a gellant, such as a Carbopole® polymer, the viscosity of the external phase composition at 21° C. is about 284,000 cP at 0.1 sec$^{-1}$, about 60,000 cP at 1 sec$^{-1}$, about 11,200 cP at 10 sec$^{-1}$, and about 6,852 cP at 20 sec$^{-1}$. In another embodiment, when using a thickening agent, such as Xanthan gum, the viscosity of the external phase composition at 21° C. is about 110,000 cP at 0.1 sec$^{-1}$, about 18,670 cP at 1 sec$^{-1}$, about 2,341 cP at 10 sec$^{-1}$, and about 1,272 cP at 20 sec$^{-1}$.

Viscosity measurements may be obtained using a suitable viscometer, including Brookfield Syncho-Lectric Model RVT Viscometer, Haake Rotovisco Model RV-12 Viscometer, or other suitable viscometers (or rheometers such as TA Instruments AR-1000N) known to those of skill in the art for measuring viscosities of Newtonian fluids or apparent viscosities of Non-Newtonian materials at low shear rates at given rotation speeds according to ASTM D1084-88, ASTM D1824-87, D2196-86 and other ASTM protocols relating to measurement of viscosity.

In forming a liposomal suspension, the external phase composition may be added to a liposomal solution containing liposomal particles or it may be added to a lyophilized (freeze-dried) preparation of liposomal particles prepared from a liposomal solution. Based on theoretical entrapment volume data, the weight percent of the liposomal particles relative to the liposomal suspension may range between about 0.96% and about 54% by weight.

When added to a liposomal solution, the external phase composition may be present in an amount between about 30% to about 75% by weight of the liposomal suspension, from about 55% to about 70% by weight of the liposomal suspension, from about 65% to about 70% by weight of the liposomal suspension, or about 65% by weight of the liposomal suspension. Additionally, the weight ratio of the liposomal solution to the external phase composition may range from about 0.002 to about 0.54. In a desired embodiment, the liposomal suspension comprises between about 35% to about 75% glycerin, more desirably between about 50% to about 65% glycerin when added to a liposomal solution. Where gellant(s), including neutralized Carbopole® are used in the external phase, the level of gellant(s) should not exceed approximately 1.0% of the liposomal suspension or visual clarity/transparency/translucency may be reduced in the liposomal suspension. Generally, the liposome preparation should be diluted with the external phase composition within 24 hours of preparation to reduce instability.

The refractive indices for liposomal suspensions may range from about 1.3 to about 1.45. By way of example, the refractive indices for liposomal suspensions comprising Newtonian fluids in the external phase composition, such as glycerin, may typically range from about 1.40 to about 1.45 and may typically range from about 1.35 to about 1.40 when using non-Newtonian fluids employing gums or gellants, including refractive indices between about 1.39 to about 1.40 for xanthan gum mixtures, and about 1.37 for external phase compositions comprising polymeric Carbopols®.

The external phase composition may further include one or more preservatives, pH adjusters, and/or water. Non-limiting examples of preservatives include phenoxyethanol, chlorphenesin, methylisothiazolinone, propylene glycol, benzyl alcohol, ethanol, methylparaben, propylparaben, ethylparaben, butylparaben, and isobutylparaben. Commercially suitable preservative preparations include those sold under the trade names Microcare® MTC (propylene glycol, chlorphenesin, and methylisothiazolinone) and Phenonip® XB (phenoxyethanol, methylparaben, propylparaben, ethylparaben). Exemplary pH adjusters include L-arginine and triethanolamine.

Applicants have unexpectedly discovered that conventional preservatives, including chelating agents, such as disodium EDTA can negatively impact on the stability of the above-described liposomal suspensions, and that sodium benzoate and various acids, including citric acid, sorbic acid, benzoic acid, and isopropyl methylphenol, can rupture the liposomal vesicles at concentration greater than 0.01%. The phenomenon of bilayer/vesicular disruption (and subsequent destabilization of the colloidal system) was confirmed by instantaneous visual opacity upon addition of citric acid to a liposomal solution as described above. Moreover, Applicants have discovered that paraben preservatives have a tendency to migrate to the bilipid membrane due to partitioning into the oil phase, which negatively impacts upon stability. In addition, parabens have been found to result in an overall increase in liposomal particle size upon aging. Applicants have further found that long term stability of liposomal suspensions of the present invention may be sacrificed when eliminating L-arginine from the water-phase composition.

Preferably, the preservatives for use in the liposomal suspensions of the present invention are free of EDTA, sodium benzoate, citric acid, sorbic acid, benzoic acid, and isopropyl methylphenol. In desired embodiments, the liposomal suspensions are additionally free of parabens. Desired preservatives for use in the liposomal suspensions of the present invention include phenoxyethanol alone, methylisothiazolinone alone, chlorphenesin alone, chlorphenesin in combination with methylisothiazolinone, or chlorphenesin in combination with methylisothiazolinone and phenoxyethanol.

Preservatives may be present in an amount between about 0.01% to about 5.00% by weight of the liposomal suspension, from about 0.01% to about 2.00%, or between about 0.01% and about 0.30% by weight of the liposomal suspension. L-arginine or triethanolamine may be present in an amount between about 0.001% to about 0.10%, desirably between about 0.001% and about 0.010%.

Active Agents

Liposomal suspensions of the present invention may further include one or more active agents (or "actives") embedded into the liposomal particles of the present invention. The active agents may include any active agents known in the art for cosmetic, therapeutic, or diagnostic applications. The actives may be hydrophobic (i.e., oil-soluble) or hydrophilic (i.e., water-soluble) in nature. Water-soluble actives may be embedded during the process of liposome preparation via "passive loading." This can be achieved by pre-dissolving the hydrophilic actives in a buffer used for hydration of the dry lipid. Any non-embedded molecule can thereafter be removed by dialyzing against the blank buffer, or by passing the dispersion through a Sephadex™ gel column. For most cosmetic and personal care products, removal of non-embedded molecules is not considered critical since there is a high cost associated with such processing, and cosmetic molecules are non-toxic at the levels they are commonly used.

By contrast with the hydrophilic actives entrapped within the core of the liposome, hydrophobic compounds typically are entrapped in the hydrophobic regions of the lipid bilayer. This type of entrapment involves a form of partitioning wherein the hydrophobic compounds are dissolved in suitable solubilizing agent(s), along with the lipid. For example, if the compound is soluble in butylene glycol, ethoxyglycol, ethanol, methanol, chloroform, toluene, ether, propylene glycol, polyethylene glycol, including polyethylene glycol 200 and polyethylene glycol 300, or medium chain triglycerides it can be dissolved along with the lipid in the solvent. While other solvents, such as ethanol and methanol can be used for solubilization of lipids and oil soluble actives, they should be removed by extraction prior to addition of the external phase composition. Applicants have discovered, for example, that solvents, such as ethanol, methanol, chloroform, toluene, or ether at concentrations above 3% can cause collapse of gellation, disruption in the density balance, or reduction in the viscosity of the external phase, thereby reducing the stability of the liposomal suspension.

By way of example, a variety of skin humectants, barrier enhancers, essential fatty acids, and vitamins may be embedded into or associated with the liposomes of the present invention. These elements help to retain moisture and further support the skin's barrier function by preventing and reversing damage thereto. Exemplary skin humectants include glycerin, sodium hyaluronate, panthenol, and amino acids.

Barrier enhancers include various skin lipids, which help to support and maintain a healthy skin barrier function. The skin barrier function is characterized by a water impermeability barrier in skin, or more specifically, the water retaining function of the stratum corneum. Lipid lamellar structures in the intercellular spaces of the stratum corneum are considered to be responsible for the water retaining properties of the stratum corneum Exemplary skin lipids contributing to maintenance of barrier function include the above described lipids contained in the oil phase composition in the above described liposomes, including phospholipids, sphingolipids, cholesterols, and phytosterols, which can be utilized to replenish critical stratum corneum lipids associated with maintaining and enhancing the skin's barrier function.

Additional barrier enhancers include hydrolyzed soybean protein and soybean protein extract. Soybean protein extract is known to inhibit the activity of an enzyme (i.e. elastase), which breaks down elastin fibers in the dermis and is released to the skin in response to UV rays, dryness, and environmental stresses generally. Treatment of skin with hydrolyzed soybean protein extract helps keep skin elastic, firm, smooth, soft, and moisturized. Hydrolyzed soybean proteins are known to stimulate production of collagen and elastin and provide firmness and elasticity to skin.

Additional barrier enhancer ingredients include essential fatty acids and vitamins. Non-limiting examples of such essential fatty acids useful in the present compositions include linoleic acid, linolenic acid, oleic acid, columbinic acid, arachidic acid, arachidonic acid, lignoceric acid, nervonic acid, eicosapentanoic acid, palmitic acid, stearic acid, and mixtures thereof. Other essential fatty acids known to those of ordinary skill in the art, such as those described in the above resources, are further contemplated as useful in the present compositions.

Essential fatty acids can be derived from a variety of sources. For example, the essential fatty acids may be provided in the liposomal suspensions from one or more oils derived from hydrophobic botanical extracts. Exemplary oils useful in this regard include various vegetable or plant oils, including but not limited to flaxseed oil, hempseed oil, cotton seed oil, pumpkin seed oil, corn oil, canola oil, linseed oil, rosemary oil, soybean oil, wheat germ oil, olive oil, grape seed oil, seabuckthorn seed oil, borage oil, macadamia integrifolia seed oil, evening primrose oil, meadowfoam seed oil, perilla ocymoides seed oil, black currant seed oil, chestnut oil, palm oil, papaya see oil, liquorice root, corn oil, grapefruit seed oil, kiwi seed oil, ligonberry seed oil, passion fruit seed oil, watermelon seed oil, rosehip seed oil, safflower oil, sunflower oil, sunflower seed oil, cottonseed oil, peanut oil, jojoba oil, sesame seed oil, poppy seed oil, vegetable oil, mixtures thereof, and hydrogenated derivatives thereof.

Alternatively, or in addition, the liposomes of the present invention may be loaded with one or more plant extracts, plant ingredients, DNA repair enzymes, and/or methylxanthines. Exemplary extracts may be derived from various plant sources, including Rosemary, *Centella, Echinacea, Alpinia*, Bearberry, Acerola Cherry Fermentate, or from the plants corresponding to the above-identified oils. Additional examples of plant extracts, plant ingredients and plant-derived oils are described in U.S. Pat. Appl. Publ. Nos. 2006/0257509 and 2007/0003536, the disclosures of which are expressly incorporated by reference herein.

The oils or extracts for use in the present invention may be present in a collective amount ranging from about 0.0001% to 1% by weight of the liposomal suspension, more desirably from about 0.0003 wt % to about 0.003 wt %.

Exemplary DNA repair enzymes include bacteriophage T4 pyrimidine dimer-specific endonuclease, *Micrococcus luteus* N-glycosylase/AP lyase, *Saccharomyces cerevisiae* N-glycosylase/apurinic-apyrimidinic lyase, *Schizosaccharomyces pombe* UV damage endonuclease (UVDE), *Chlorella* virus isolate PBCV-1 pyrimidine dimer-specific glycosylase, and *Anacystis nidulans* photolyase. Additional DNA repair enzymes are described in U.S. Pat. Appl. Publ. Nos. 2006/0257509, the disclosures of which are expressly incorporated by reference herein. The DNA repair enzymes may be present in a collective amount ranging from about 0.01% to about 10% by weight of the liposomal suspension, more desirably from about 0.1% to about 3% by weight.

Exemplary vitamins include the above-described antioxidants, as well as lipophilic vitamins, such as vitamin A, including free acids or derivatives thereof and precursors thereof, including retinoids, such as retinol, retinal, and retinyl esters, such as retinyl acetate, retinyl butyrate, retinyl propionate, retinyl octanoate, retinyl laurate, retinyl palmitate, retinyl oleate, and retinyl linoleate; and carotenoids; B-complex vitamins, including B1: thiamine, B2: riboflavin, B6: pyridoxin, panthenol, and pantothenic acid; vitamin B12 and combinations thereof; vitamin D, biotin, vitamin K, water-soluble derivatives thereof, and the like.

Topical administration of methylxanthines, such as caffeine, is believed to reduce the deleterious effects of DNA damage caused by exposure of skin to ultraviolet or solar radiation. Specifically, topical administration of caffeine to the mice skin after irradiation with ultraviolet light, was shown to decrease the number of nonmalignant and malignant skin tumors (Lu et al., Proc. Natl. Acad. Sci. USA 99(19):12455-60, 2002), diminish photodamage, and promote the elimination of DNA-damaged keratinocytes (Koo et al., Br. J. Dermatol., 156(5):957-64, 2007). In addition, methylxanthines, like caffeine are believed to act as "sunless" tanning agents modulating the activity of biochemical pathways involved in melanogenesis, presumably by their ability to inhibit cyclic-AMP phosphodiesterase and enhance the production of melanin in melanocytes, alone or in combination with tanning stimulants like ultraviolet or solar radiation.

Exemplary methylxanthines for use in the present invention include caffeine (1,3,7-trimethylxanthine), theophylline (1,3-dimethylxanthine), aminophylline, theobromine (3,7-dimethylxanthine), paraxanthine, isobutylmethyl xanthine, butymethylxanthine, as well as analogs, derivatives, and combinations thereof. In a particular embodiment, a methylxanthine, such as caffeine, will be present at a weight concentration of about 0.01% to about 0.30%.

Other additives that may be included in the liposomal suspensions of the present invention will be apparent to those of skill in the art and are included within the scope of the present invention.

In skin care or cosmetic products, the liposomal suspensions of the present invention can be incorporated into cosmetically suitable matrix to form a cosmetic formulation in the form of a cream, lotion, gel, serum, tonic, emulsion, paste, or spray for topical administration.

Methods for Producing Liposomes

In another aspect, the present invention provides a method for producing a stable, transparent to translucent, unilamellar liposomal suspension as described above. In one embodiment, a method for producing a stable, transparent to translucent, unilamellar liposomal suspension includes: (a) preparing an oil-soluble composition comprising a coupling agent, at least one phospholipid, a rigidity enhancer, and an antioxidant; (b) preparing a water-soluble composition; (c) combining the water-soluble composition with the oil-soluble composition to form a multilamellar, multivesicular liposome preparation; (d) converting the multilamellar, multivesicular liposome preparation to a unilamellar liposome preparation; and (e) adding the unilamellar liposome preparation to an external phase composition having a density within a range of about 0.95 g/cc to about 1.25 g/cc. The method will typically result in a liposomal suspension comprising a uniform plurality of unilamellar liposomal particles having a mean particle size between about 50 to about 290 nm, wherein the liposomal suspension has a refractive index between 1.30 and 1.45 and retains its stability in neat form within an amber glass jar, colorless glass jar, or opaque plastic container at about 4° C. to about 50° C. for a period of at least 30 days, or at 21° C. for a period of at least 180 days, or longer.

In one embodiment, the oil-soluble composition may be prepared by sequentially adding at least one coupling agent, at least one phospholipid, at least one rigidity enhancer, and/or at least one antioxidant to form a batch composition. The batch composition may be agitated and heated to temperature sufficient to dissolve the components (for example, 190-210° F.). Upon cooling, one or more temperature-sensitive oil-soluble components, including oil-soluble actives may be added. The batch composition may then be cooled and maintained (and agitated) at a temperature between about 75-85° F. for phase combination with the water-soluble composition. The water-soluble composition and the oil-soluble composition (with or without water-soluble and/or oil-soluble actives) may be mixed in an agitator (at for example, 50 rpm for 10-15 minutes). A multilamellar, multivesicular liposomal particle composition may be formed and then converted to a unilamellar liposomal particle composition using a suitable conversion process, such as high pressure microfluidization, extrusion, high speed shearing, milling, sonication, selective microchannel filtration or homogenization. An external phase composition may be prepared by sequentially mixing together one or more and dissolving the contents under agitation and adding the contents of the external phase composition to a liposome preparation as described above.

Because the biological activity of certain active ingredients may be compromised after being subjected to temperatures in the oil-soluble batch composition of about 200° F., for example, certain active ingredients, including botanical substances (such as *Centella asiatica* extract), may be solubilized in the water-soluble composition under more reduced temperature conditions or they may added (and solubilized) in the oil-soluble batch composition upon further cooling.

A number of methodologies may be employed for converting a multilamellar, multivesicular liposome preparation to a unilamellar liposome preparation. These include high pressure microfluidization, extrusion, high speed shearing, milling, sonication, selective microchannel filtration, and homogenization.

Microfluidization provides a desirable method for producing unilamellar liposome preparations, particularly in view of its capacity for producing liposome preparations in bulk quantities. Microfluidization involves introduction of slurry-like concentrated lipid/water dispersions in a microfluidizer which pumps the dispersions at a very high pressure (10,000 to 20,000 psi) through microchannels of 1-5 μm in diameter. The microchannels are split and impinged upon each other to enhance droplet size reduction and energy input. Fluid moving at a very high velocity is split into two streams by forcing it through two defined microchannels. Massive cavitation is experienced though a rapid pressure differential upon entry of the fluid through the tiny orifice of the microfluidics chamber. A similar pressure differential is obtained through conventional homogenization. The two streams are then made to collide together at right-angles at very high velocity. The tremendous energy imparted by the high pressure differential and high velocity causes the lipids to self-assemble into liposomes. The fluid collected at the end may be re-passed through the microfluidizer one to four times until a homogeneous-looking dispersion, and unimodal, uniform particle size distribution is obtained. Suitable microfluidic devices for producing the liposome preparations in accordance with the present invention include Microfluidics Models M110Y and M210EH (Microfluidics Corp., Newton, Mass.)

Alternatively, the unilamellar liposomes of the present invention can be also created by sonicating phospholipids in water. Low shear rates create multilamellar liposomes, which have many layers like an onion. Continued high-shear sonication tends to form smaller unilamellar liposomes.

In a further aspect, the present invention includes a method for preparing a cosmetic formulation, wherein a liposomal suspension of the present invention is combined with a cosmetically suitable matrix to form a cosmetic formulation in the form of a cream, lotion, gel, serum, tonic, emulsion, paste, or spray.

Transmission electron microscopy (TEM) provides a means for characterizing the size, integrity, and stability of the liposomes. A commonly used method of sample preparation includes applying a drop of liposome suspension diluted 1:5 into a plastic-coated grid, negatively staining the material with phosphotungstic acid or ammonium molybdate, thereby producing a monolayer of liposomes embedded in the negative stain.

More specifically a sample may be prepared for TEM analysis as follows: 1% aqueous agarose (w/v) is poured into plastic Petri dishes and air-dried at room temperature for 10 minutes. Formvar or collodion coated grids are made hydrophilic by glow discharge and the grids are placed on Whatman no. 1 filter paper. One drop of the sample suspension is placed on each grid. When most of the liquid is absorbed at the periphery of the grid by the filter paper, the grids are transferred to the agarose plates for 30 minutes to 1 hour to facilitate salt and liquid diffusion into the agarose.

The unstained grids are viewed and photographed using a Zeiss-902 with ESI. Typically, the liposomes will appear as discrete round structures without evidence of significant clumping.

Liposomal particle sizes and stability may be evaluated, for example, by evaluating the sizes and structures of liposomes in an aqueous solution or in a cream formulation both prior to or following storage in an amber glass jar, colorless glass jar, or opaque plastic container for 1-12 months after storage, or later. Liposomal particle sizes and stability may be evaluated using suitable laser light scattering (e.g., Nanotrac® or Microtrac®), multiple light scattering, kinetic stability analyzer (Turbiscan® TLab Expert), and/or transmission electron microscopy devices and methodologies as known to those of skill in the art.

In one aspect, laser light scattering may be used for particle size quantitation. For example, the Nanotrac® utilizes a "controlled reference" dynamic light scattering approach, which utilizes a 780 nm wavelength laser diode shining light through a sapphire filter window into a diluted sample dispersion media. Laser light (in a scattered pattern of shifted frequencies) is reflected back through the sapphire window into an optical splitter that is received by a photodetector. The shifted frequencies of the scattered light represent the combination of the "controlled reference", which is light reflected by the sapphire filter (of known un-shifted frequency), in conjunction with the influence of the velocity of suspended sample particles experiencing Brownian motion. The laser is frequency shifted according to the "Doppler effect", which is proportional to the motion velocity of the distribution of particles of interest. The detector output signals are then amplified, filtered, digitized and mathematically analyzed to quantify the particle size distribution.

Figure 5:
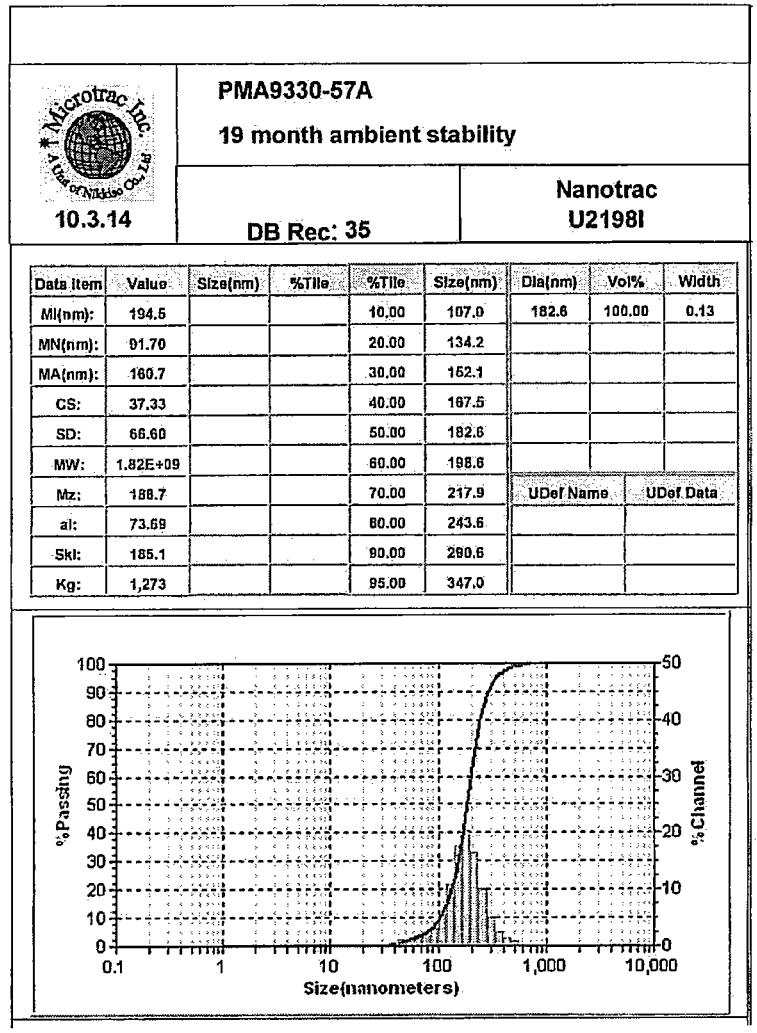
FIG. 5 is a particle size analysis of a liposomal formulation according to an embodiment of Table 4 after 19 months of shelf life under ambient temperature conditions.

A stable liposomal system exhibits a uniform, unimodal distribution of particles upon aging when subjected to reduced or elevated temperatures. A bimodal or trimodal distribution occurs when the particles coalesce or flocculate leading to rupture of their entrapped contents and full-scale creaming or sedimentation of the entire microstructure/colloidal system. A liposomal suspension according to the present invention may retain its stability in neat form within an amber glass jar, colorless glass jar, or opaque plastic container at about 4° C. to about 50° C. for a period of at least 30 days, at least about 2 months, at least about 3 months, at least about 6 months, at least about 19 months, or longer. As shown in FIG. 5 below, liposomal formulations of the present invention were found to retain their stability and unimodal particle distribution under ambient room temperature conditions for at least 19 months, as reflected in a unimodal particle size distribution characterized by a mean particle size of about 157 nm and a size range between about 54 nm and about 521 nm.

A Turbiscan Accelerated Kinetic Stability Analyzer can provide a traceable, quantitative method for early prediction of instability of colloidal systems. The Turbiscan Analyzer employs multiple light scattering to detect the level of transmitted and backscattered light as a function of sample depth for colloidal systems ranging in appearance from transparent to opaque. The Turbiscan instrument consists of a near infrared laser diode which shines photons of light throughout the depth of a small (1 cm×8 cm) cylindrical glass cell filled with a sample. The photons of light emerge (1) from the sample in a scattered pattern, which are detected simultaneously by transmission (for transparency) and backscatter (for opacity) detectors. The ratio of backscattered to transmitted light is collected as a "fingerprint" scan according to user-defined time intervals. Kinetic results of the superimposed data scans show the degree of homogeneity of the suspension, emulsion or foam of interest.

Relative to the term "stability" in the present invention, a "backscatter kinetic result" may be defined as the relative change in backscattered light as a function of time interval defined by the user. Each scan of backscattered light for the product changes with each time interval scanned by the laser. This change in backscattered light relates to the migration of particles within the system. In a stable liposomal suspension, a laser scan of backscattered light will change little relative to the initial scan of backscattered light. Relative to the present invention, a backscatter kinetic result of less than 2.0% depicts a stable liposomal solution or suspension under the selected temperature conditions and user-defined time intervals. For the liposomal systems of the present invention, the backscatter kinetic results were approximately 0.2 to 1.0% when exposed to temperatures between 25° C. to 50° C. over a 16 hour period. Early indications of instability can be detected in a period as short as 4-8 hours for colloidal systems.

Modes of Administration

The liposomal suspensions of the present invention are generally designed for topical administration. Generally, the compositions of the present invention are administered at least on a daily basis. Administration of the compositions of the invention may continue for any suitable period of time. It should be appreciated that the degree of cosmetic enhancement and degree of maintenance, improvement, restoration, or repair will vary directly with the total amount and frequency of composition used.

Useful dosage forms can be prepared by methods and techniques that will be well understood by those of skill in the art and may include the use of additional ingredients in producing appropriate dosage forms. In one example, a liposomal suspension of the present invention is topically administered at least once a day. In another example, a liposomal suspension is administered twice daily. In a further example, the formulation may be administered three to five times daily. Generally, there is no limit on the amount of the formulation that may be administered daily.

The present invention also includes methods of treating skin by topically applying the liposomal suspensions of the present invention. In use, a small quantity of the composition, for example from 1 to 100 ml, may be applied to exposed areas of the skin, from a suitable container or applicator and, if necessary, it is then spread over and/or rubbed into the skin using the hand or fingers or a suitable device.

In one embodiment, the present invention provides a method for preventing, arresting, reversing, ameliorating, diminishing, reducing, or improving a sign of aging, in which a composition of the present invention is topically applied to skin in a cosmetically effective amount sufficient to prevent, arrest, reverse ameliorate, diminish, reduce, or improve a sign of aging in skin. Exemplary signs of aging include, but are not limited to, facial lines, fine lines, wrinkles, crow's feet, dark eye circles, blemishes, age spots, stretch marks, weakened skin barrier repair properties, or combinations thereof.

In another embodiment, the present invention provides a method for improving the aesthetic appearance of skin, in which a composition of the present invention is topically applied to skin in a cosmetically effective amount sufficient to improve the aesthetic appearance of the skin. The improvements may relate to skin thickness, elasticity, resiliency, moisturization, tone, texture, radiance, luster, brightness, clarity, contour, uniformity, firmness, tautness, suppleness, softness, sensitivity, pore size, reduction in water loss, or combinations thereof.

The improvements may further relate to improving adverse skin conditions affected by, resulting in or resulting from the group consisting of psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

The signs of aging or adverse skin conditions may result from free radical damage, environmental agents, pollutants, diet, chronological aging, premature aging, hormonal aging, photo-aging, or combinations thereof. Accordingly, the present compositions and methods selected for improved anti-aging characteristics or adverse skin conditions may employ topical application of active ingredients inhibiting enzymes or mediators that accelerate or facilitate aging, damage, formation of free radicals, or breakdown of skin elements, including, but not limited to metalloproteinases, collagenases, elastases, hyaluronidases, and proteases. The active ingredients may have anti-oxidant activity, free radical scavenging or anti-inflammatory activity, and/or they may inhibit breakdown of collagen, elastin, fibronectin, hyaluronic acid, glycosaminoglycans (GAG), or other extracellular matrix elements or regulatory enzymes or mediators of the NF-kB signal transduction pathway. The active agents may also inhibit other signal transduction pathways associated with aging, including the mediators and regulators associated with these pathways, or combinations thereof.

In addition to improving the aesthetic or cosmetic appearance of skin, the topical compositions of the present invention may be topically applied to enhance the general health, vitality and appearance of the skin. For example, the present composition may be applied to skin to improve microcirculation, communication among skin cells, replenishment of essential nutrients or skin constituents, or to improve the metabolism, proliferation, multiplication, turnover and/or exfoliation of skin cells.

Exfoliation may be carried out with or without the use of alpha- or beta hydroxy acids or other exfoliants, or combinations thereof by topical application to skin. When using exfoliating agents in the compositions of the present invention, sufficient anti-irritant or anti-inflammatory agents are included to neutralize the potential irritation associated with exfoliating agents in the absence of such neutralizing agents.

It is intended that the foregoing detailed description be regarded as illustrative rather than limiting. The present invention is further illustrated by the following experimental investigations and examples, which should not be construed as limiting. Further, the liposomal suspensions in Tables 3-6 are exemplary formulations, whose compositional ingredients and amounts may be modified in accordance with the teachings above.

EXAMPLE 1

Preparation of a Liposomal Suspension

In an exemplary method for preparing a liposomal suspension according to the present invention, an oil-soluble composition was prepared by sequentially adding to a scrapewall turbine tank Phospholipon® 85, ceramide IIIB, beta-sitosterol, and butylene glycol. Scrapewall agitation at 40 rpm was initiated and the batch composition was heated to a temperature (190-210° F.) sufficient to dissolve the components. The composition was cooled, and tocopherol was added when the batch temperature dropped to 170° F. The batch composition was then cooled to, and maintained at, a temperature between 75-85° F. for phase combination with the water-soluble composition. While agitating the scrapewall at 50 rpm, water was slowly added to the oil-soluble composition using an air powered gear pump at a rate of 8-10 lb/min. The water-soluble and oil-soluble components were mixed for 10-15 min. with the turbine agitator at 50 rpm. The resulting multilamellar, multivesicular liposomal particle composition was then subjected to 1-4 passes at 12,000-15,000 psi in a microfluidizer (Microfluidics M110Y and M210EH) using 80-100 psi in-feed pressure to form a unilamellar liposomal particle composition. An external phase composition was prepared by sequentially mixing together in a scrapewall turbine tank glycerin, methylparaben, arginine, and water and dissolving the contents at 145-155° F. for about 20 min. under agitation (scrapewall at 30 rpm; turbine at 300-350 rpm). Upon cooling to 140° F., additional preservatives were added to external phase composition. Then, upon further cooling, the microfluidized unilamellar particle composition was added to the external phase composition and mixed for 15 min. at 75-90° F.

The resulting liposomal suspension containing 60% glycerin had a refractive index of 1.4 and was stable at temperatures between 4° C. and 60° C. for at least 6 months. The formulation was further evaluated by Transmission Electron Microscope (TEM) analysis (FIGS. 1A-1C), which confirmed the production of structurally intact unilamellar liposomes (FIGS. 1B, 1C).

Figure 1B:
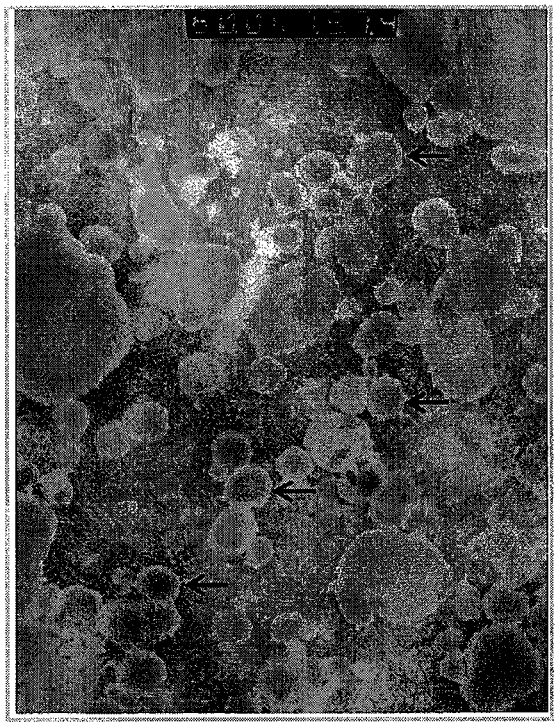
FIGS. 1B and 1C are TEM micrographs of the liposomal suspension in FIG. 1A at 180,000× magnification. Exemplary lipid bilayers are identified by arrows in FIGS. 1B and 1C.
Figure 1C:
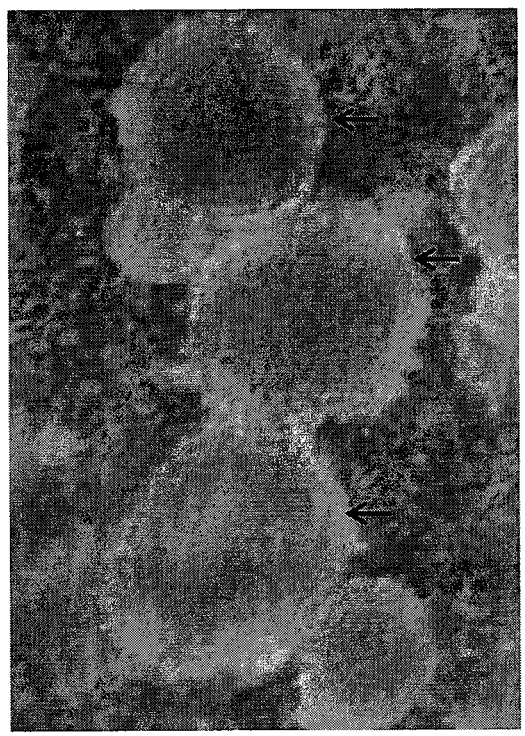

Table 1 shows a particle size analysis of a liposomal formulation according to FIGS. 1A-1C following 2 or 3 passes through the microfluidizer at various time intervals after preparation (initial, 1 month, 2 months, 3 months, and 6 months) under varying temperature storage conditions (40° F., ambient, and 120° F.) by dynamic laser light scattering using a Nanotrac® N150 Submicron Particle Size Analyzer (Microtrac Inc., Montgomeryville, Pa.). Each of the 25 conditions listed includes particle size calculations for 75 different tests based on 3 scans (histograms) for each condition tested. As shown in Table 1, a cosmetic formulation comprising the liposomal suspension was characterized by a particle size range between 56 nm to 333 nm, and a median particle size of about 140 nm following 6 months of storage under ambient temperature conditions.

Figure 2:
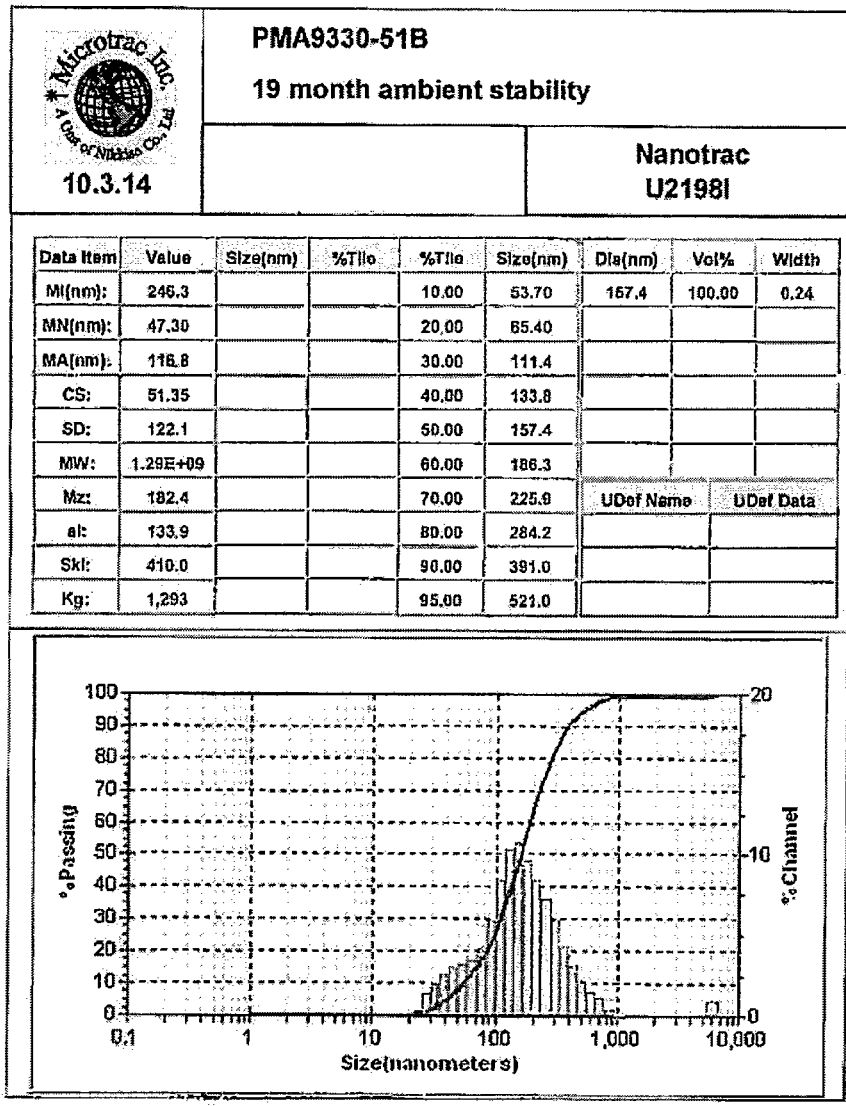
FIG. 2 is a particle size analysis of another embodiment according to the liposomal formulation depicted in FIGS. 1A-1C after 19 months of shelf life.

FIG. 2 shows the resulting unimodal, particle size distribution of a liposomal suspension according to Example 1 after 19 months of shelf life under ambient temperature conditions. FIG. 2 shows a mean particle size of about 157 nm and a size range between about 54 to about 521 nm.

EXAMPLE 2

Table 2 depicts a liposomal suspension made by the process described in EXAMPLE 1.

TABLE 2

| Ingredients | Amount (percent) |
| --- | --- |
| Oil-Soluble Composition | |
| Phospholipid(s) | 1.0-10.0 |
| Ceramide(s) | 0.01-1.0 |
| Phytosterol(s) | 0.01-1.0 |
| Coupling agent(s) | 1.0-10.0 |
| Antioxidant(s) | 0.01-1.0 |
| Water-Soluble Composition | |
| Water | 5.0-60.0 |
| External Phase Composition | |
| Viscosity promoting agent(s) | 35.0-70.0 |
| Preservative(s) | 0.0-5.0 |

TABLE 1

Particle Size Analysis for Liposomal Formulation, Reference#PMA9330-87

| | | 2G T = 40 °F. | | 2G T = Ambient | | 2G T = 120 °F. | | 3G T = 40 °F. | | 3G T = Ambient | | 3G T = 120 °F. | |
| --- | --- | --- | --- | --- | --- | --- | --- | --- | --- | --- | --- | --- | --- |
| | Range | size [nm] | vol % | size [nm] | vol % | size [nm] | vol % | size [nm] | vol % | size [nm] | vol % | size [nm] | vol % |
| Initial | Low | 25.55 | | 25.55 | | 25.55 | | 18.06 | | 18.06 | | 18.06 | |
| | High | 486 | | 486 | | 486 | | 486 | | 486 | | 486 | |
| | Mean | 143.1 | 100 | 143.1 | 100 | 143.1 | 100 | 125 | 100 | 125 | 100 | 125 | 100 |
| 1 month | Low | 18.06 | | 30.4 | | 25.55 | | 25.55 | | 18.06 | | 25.55 | |
| | High | 1156 | | 2312 | | 578 | | 687 | | 578 | | 687 | |
| | Mean | 181.2 | 100 | 193.1 | 100 | 175.8 | 100 | 151.4 | 100 | 133.9 | 100 | 132 | 100 |
| 2 months | Low | 18.06 | | 25.55 | | 36.1 | | 18.06 | | 18.06 | | 25.55 | |
| | High | 818 | | 578 | | 818 | | 687 | | 486 | | 1156 | |
| | Mean | 154.2 | 100 | 153.9 | 100 | 154.3 | 100 | 125.8 | 100 | 143.3 | 100 | 134 | 100 |
| 3 months | Low | 18.06 | | 25.55 | | 36.1 | | 15.19 | | 18.06 | | 30.4 | |
| | High | 578 | | 972 | | 578 | | 578 | | 486 | | 578 | |
| | Mean | 169.2 | 100 | 156.1 | 100 | 174.3 | 100 | 134.1 | 100 | 143.1 | 100 | 158 | 100 |
| 6 months | Low | | | | | | | | | 56 | | | |
| | High | | | | | | | | | 333 | | | |
| | Mean | | | | | | | | | 140 | 100 | | |

2G = 2 passes through microfluidizer
3G = 3 passes through microfluidizer
**Cosmetic Formulations are only tested for physical properties under ambient conditions beyond 3 months of shelf life.

EXAMPLE 3

Table 3 depicts a liposomal suspension formed by the process described in EXAMPLE 1.

TABLE 3

| Ingredients | Amount (percent) |
|---|---|
| Oil-Soluble Composition | |
| Lecithin | 4.000 |
| Ceramide IIIB | 0.150 |
| Beta-sitosterol | 0.100 |
| Butylene glycol | 4.000 |
| Tocopherol | 0.010 |
| Water-Soluble Composition | |
| Water | 27.000 |
| External Phase Composition | |
| Glycerin | 60.483 |
| Arginine | 0.007 |
| Water | 2.000 |
| Preservative(s) | 2.250 |

EXAMPLE 4

Figure 3:
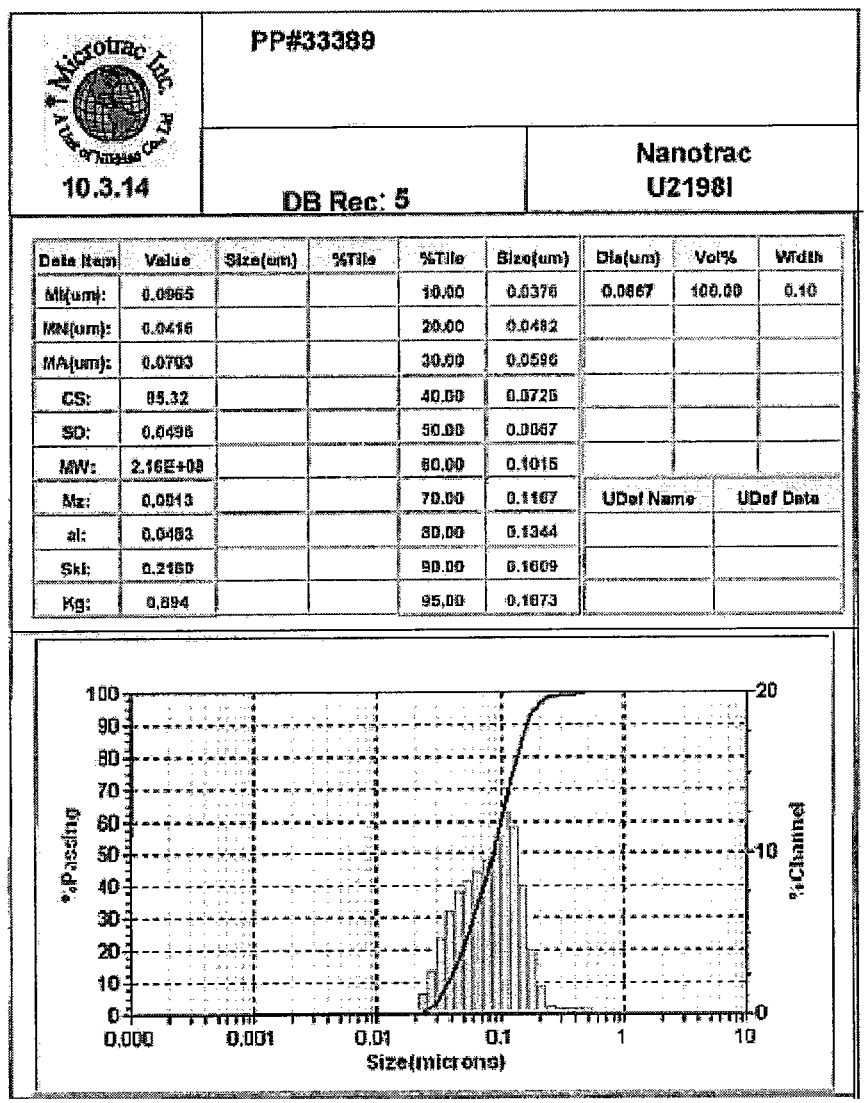
FIG. 3 is a particle size analysis of a liposomal suspension according to an embodiment of Table 4 after 2.5 months of shelf life in ambient temperature conditions by dynamic laser light scattering using a Nanotrac® N150 Submicron Particle Size Analyzer.
Figure 4:
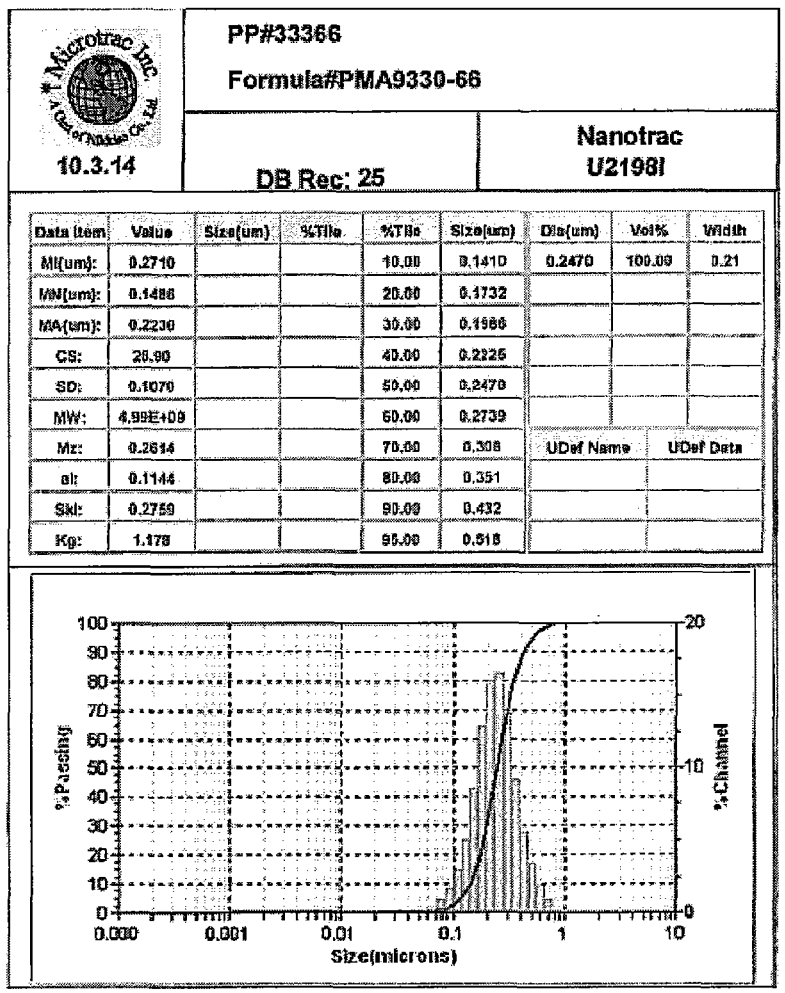
FIG. 4 is a particle size analysis of a liposomal suspension according to an embodiment of Table 4 after 2.5 months of shelf life under ambient temperature conditions.

Table 4 depicts a liposomal suspension formed by the general process described in EXAMPLE 1 in conjunction with several ingredient modifications as indicated below. FIGS. 3 and 4 display the resulting unimodal, particle size distribution of two liposomal suspensions according to Table 4 with different preservative combinations after 2.5 months of shelf life under ambient temperature conditions. The liposomal solution in FIG. 3 was passed through a microfluidizer 4 times; the liposomal solution in FIG. 4 was passed through a microfluidizer 2 times. FIG. 3 shows a mean particle size of about 87 nm and a size range between about 38 to about 187 nm for a paraben-free suspension employing phenoxyethanol, propylene glycol, chlorphenesin, and methylisothiazolinone. FIG. 4 shows a mean particle size of about 247 nm and a size range between about 141 nm to about 518 nm for a suspension employing phenoxyethanol in combination with various parabens, including methylparaben, propylparaben, and ethylparaben. FIG. 5 shows maintenance of a unimodal particle size distribution of a liposomal suspension according to Table 4 under ambient room temperature conditions for at least 19 months. In particular, FIG. 5 shows a unimodal particle size distribution characterized by a mean particle size of about 157 nm and a size range between about 54 nm and about 521 nm.

TABLE 4

| Ingredients | Amount (percent) |
|---|---|
| Oil-Soluble Composition | |
| Lecithin | 4.000 |
| Ceramide IIIB | 0.150 |
| Beta-sitosterol | 0.100 |
| Butylene glycol | 4.000 |
| Tocopherol | 0.010 |
| Meadowfoam Seed Oil | 0.150 |
| Soybean Oil | 0.200 |
| Evening Primrose Oil | 0.050 |
| *Perilla Ocymoides* Seed Oil | 0.050 |

TABLE 4-continued

| Ingredients | Amount (percent) |
|---|---|
| Omega Plus ® (sunflower seed oil, corn oil, sesame seed oil, macadamia seed oil, olive oil) | 0.050 |
| Tocopheryl acetate | 0.050 |
| Water-Soluble Composition | |
| Water | 27.000 |
| External Phase Composition | |
| Glycerin | 58.458 |
| Arginine | 0.007 |
| Water | 2.000 |
| Preservative(s) | 3.250-3.700 |

EXAMPLE 5

Figure 6:
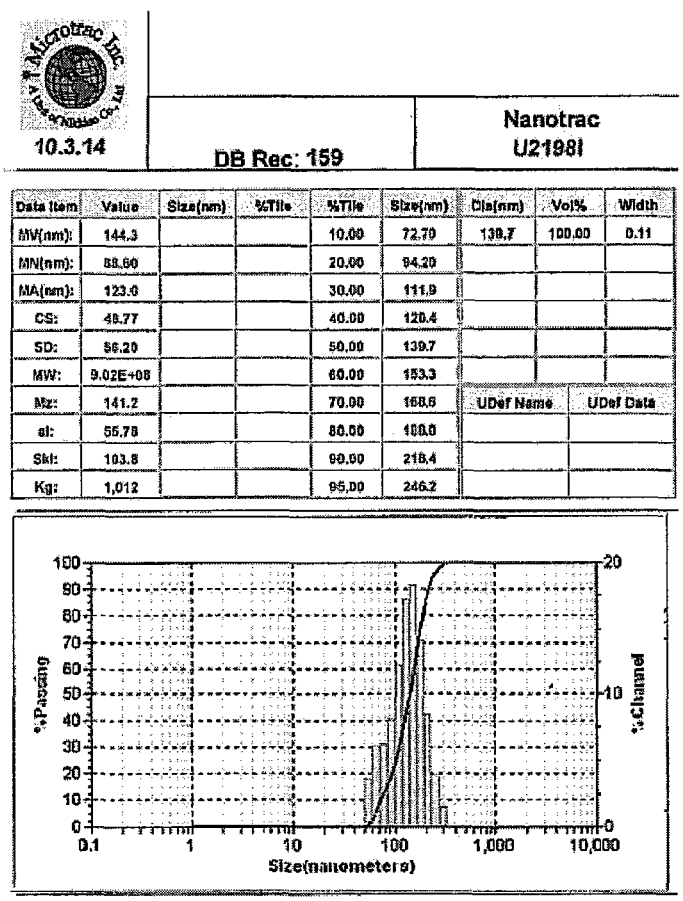
FIG. 6 is a particle size analysis of a liposomal suspension according to Table 5 after 2.5 months of shelf life under ambient temperature conditions.

Table 5 depicts a liposomal suspension formed by the general process described in EXAMPLE 1 in conjunction with several ingredient modifications as indicated below. FIG. 6 displays the resulting unimodal, particle size distribution of the Table 5 suspension after 2.5 months of shelf life under ambient temperature conditions in which the liposomal solution was passed through a microfluidizer 2 times.

TABLE 5

| Ingredients | Amount (percent) |
|---|---|
| Oil-Soluble Composition | |
| Lecithin | 4.000 |
| Ceramide IIIB | 0.150 |
| Beta-sitosterol | 0.100 |
| Butylene glycol | 4.000 |
| Tocopherol | 0.010 |
| Meadowfoam Seed Oil | 0.150 |
| Soybean Oil | 0.200 |
| Evening Primrose Oil | 0.050 |
| *Perilla Ocymoides* Seed Oil | 0.050 |
| Omega Plus ® (sunflower seed oil, corn oil, sesame seed oil, macadamia seed oil, olive oil) | 0.050 |
| Tocopheryl acetate | 0.050 |
| Tetrahexyldecyl ascorbate | 0.025 |
| Water-Soluble Composition | |
| Butylene glycol | 4.000 |
| *Centella asiatica* extract | 0.100 |
| Caffeine | 0.100 |
| Water | 22.800 |
| External Phase Composition | |
| Glycerin | 60.158 |
| Arginine | 0.007 |
| Water | 2.000 |
| Preservative(s) | 2.000 |

EXAMPLE 6

Figure 7:
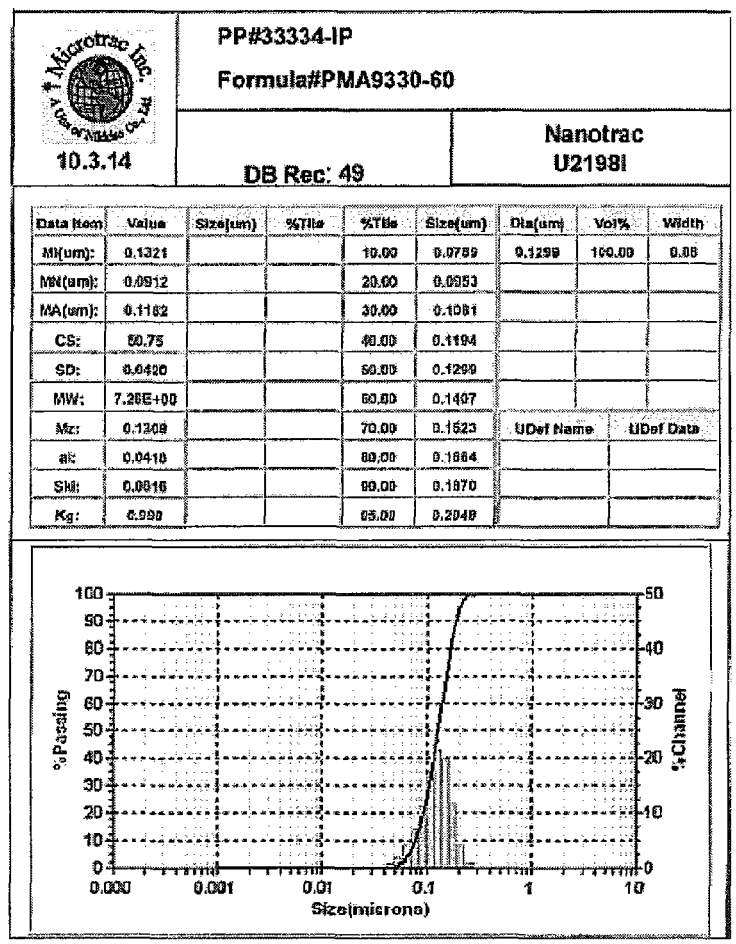
FIG. 7 is a particle size analysis of a liposomal suspension according to Table 6 after 2.5 months of shelf life under ambient temperature conditions.

Table 6 depicts a liposomal suspension applying the general process described in EXAMPLE 1 in conjunction with several ingredient modifications as indicated below. FIG. 7 displays the resulting unimodal particle size distribution of the Table 6 suspension after 2.5 months of shelf life under ambient temperature conditions.

TABLE 6

| Ingredients | Amount (percent) |
|---|---|
| Oil-Soluble Composition | |
| Lecithin | 3.000 |
| Beta-sitosterol | 0.100 |
| Butylene glycol | 3.000 |
| Tetrahexyldecyl ascorbate | 0.100 |
| Tocopheryl acetate | 0.200 |
| Water-Soluble Composition | |
| Water | 27.000 |
| Acerola Cherry Ferment | 0.100 |
| Bearberry extract | 6.690 |
| External Phase Composition | |
| Glycerin | 37.500 |
| Xanthan gum | 0.800 |
| Water | 26.950 |
| Preservative(s) | 1.000 |

EXAMPLE 7

Liposomal Cream Formulations

Figure 8:
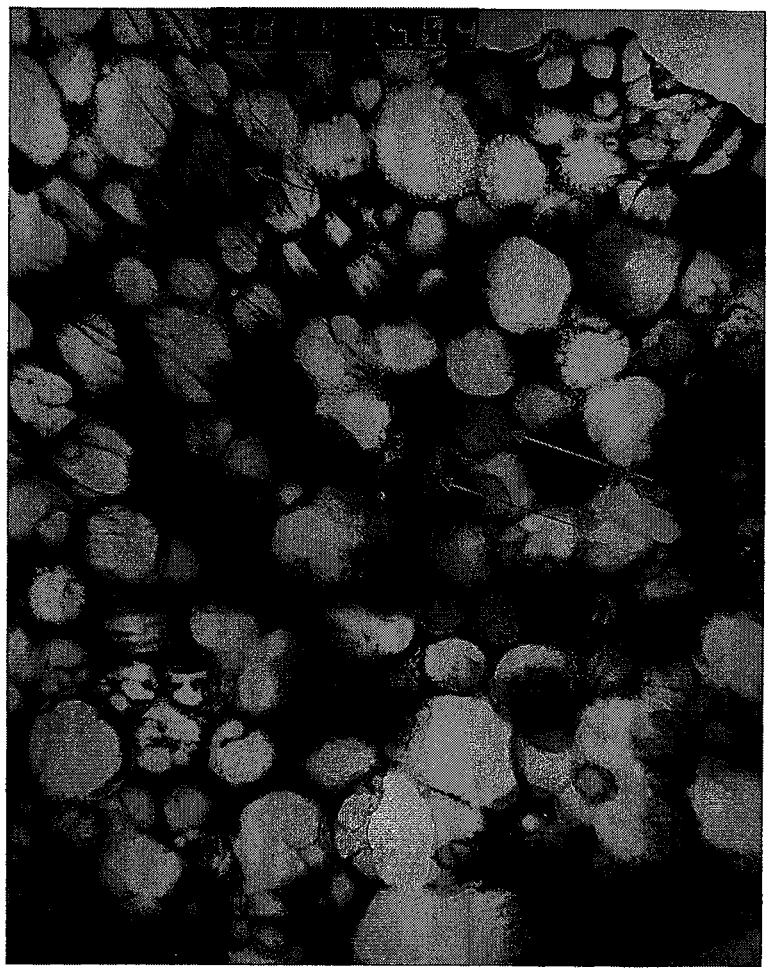
FIG. 8 is a TEM micrograph of a liposomal cream formulation taken using a Zeiss-902 electron microscope at 11,430× magnification. Liposomes are identified by arrows.
Figure 9:
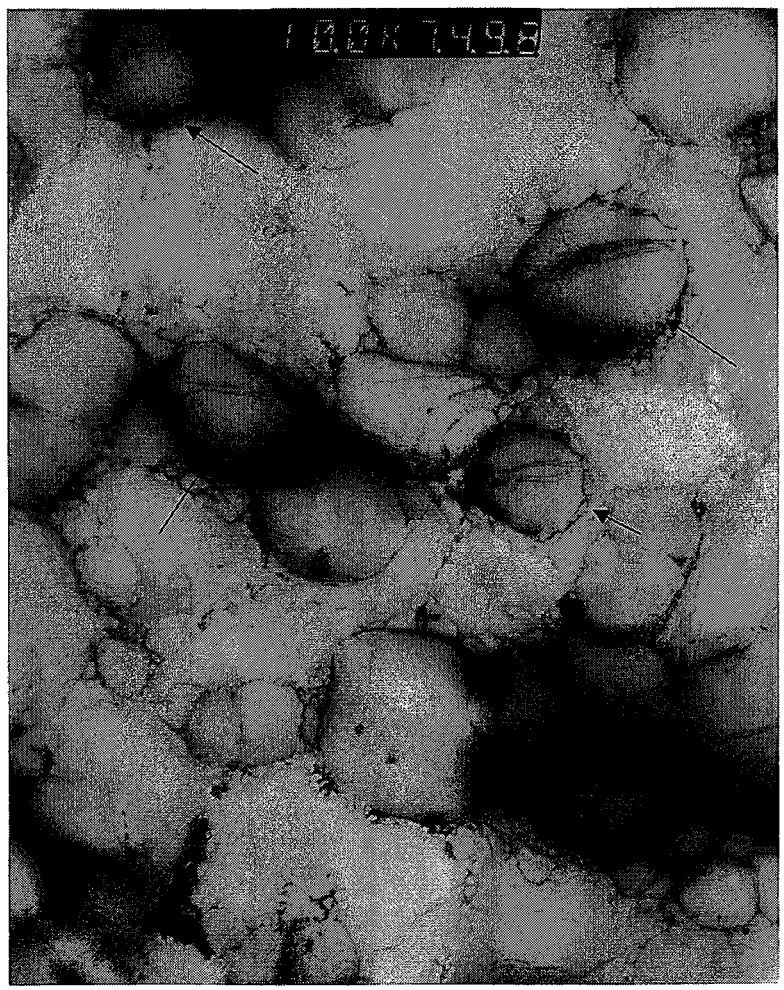
FIG. 9 is a TEM micrograph of a liposomal cream formulation taken using a Zeiss-902 electron microscope at 30,000× magnification. Liposomes are identified by arrows.

FIG. 8 is a TEM micrograph of a liposomal cream formulation at 11,430× magnification. FIG. 9 is a TEM micrograph of a liposomal cream formulation taken using a Zeiss-902 electron microscope at 30,000× magnification. Liposomes are identified by arrows. Liposomes are identified by arrows. In FIGS. 8 and 9, a liposomal suspension was diluted 1:5 in deionized water and mixed until homogeneous.

The invention claimed is:

1. A method for preparing a stable translucent to transparent unilamellar liposomal suspension comprising:
 a. preparing an oil-soluble composition comprising
  i. at least one phospholipid,
  ii. a rigidity enhancer in an amount from about 0.02% to about 1% of the liposomal suspension and being selected from the group consisting of a sphingolipid, a ceramide, a phytosterol, a sterol and a combination thereof,
  iii. an antioxidant selected from the group consisting of tocopherol, derivatives of tocopherol, alpha tocopherol, tocopheryl acetate, tocopherol succinate, ascorbic acid, derivatives of ascorbic acid, tetrahexyldecyl ascorbate, butylated hydroxyl toluene, butylated hydroxyanisole, and mixtures thereof, and
  iv. a coupling agent for solubilizing immiscible phases of differing polarity and having a dielectric constant of about 10.5 or greater at 23° C., wherein the coupling agent is selected from the group consisting of butylene glycol, propylene glycol, hexylene glycol, and polyethylene glycol, and mixtures thereof;
 b. preparing a water-soluble composition;
 c. combining with agitation the water-soluble composition and the oil-soluble composition to form a multilamellar and multivesicular liposome preparation, wherein the water soluble composition is present in an amount from about 67% to about 95% by weight of the liposome preparation and the oil soluble composition is present in an amount from about 5% to about 33% by weight of the liposome preparation;
 d. converting the multilamellar and multivesicular liposome preparation to a unilamellar liposome preparation by one of high pressure microfluidization, extrusion, high speed shearing, milling, sonication, selective microchannel filtration or homogenization, wherein the unilamellar liposome preparation comprises a plurality of unilamellar liposomal particles having a unimodal size distribution with a mean particle size between about 50 to about 290 nm; and
 e. adding the unilamellar liposome preparation to an external phase composition that includes a viscosity promoting agent selected from thickening agents to provide the unilamellar liposomal suspension, wherein the external phase composition has a density within a range of about 1.05 g/cc to about 1.25 g/cc and a viscosity between about 2.5 cP and about 40,000 cP at a shear rate of 10 sec$^{-1}$ at 21° C.; and,
 wherein the liposomal suspension is translucent to transparent, has a refractive index between 1.30 and 1.45 and retains its stability in neat form at temperatures between about 4° C. to about 50° C. for a period of at least 30 days, or at 21° C. for a period of at least 180 days.

2. The method of claim 1, wherein the coupling agent is butylene glycol.

3. The method of claim 1, wherein the at least one phospholipid comprises a glycerophospholipid with varying fatty acyl moieties or a sphingolipid.

4. The method of claim 1, wherein the at least one phospholipid comprises a phospholipid preparation comprising phosphatidylcholine at a concentration of between about 80% to about 95% by weight of the phospholipid preparation.

5. The method of claim 1, comprising at least two rigidity enhancers, including at least one phytosterol and at least one member selected from the group consisting of ceramide, sphingosine, and phytosphingosine.

6. The method of claim 1, wherein the weight ratio of the liposome preparation to the external phase composition is from about 0.002 to about 0.54.

7. The method of claim 1, wherein the external phase comprises glycerin at a concentration between about 35% to about 75% of the liposomal suspension.

8. The method of claim 1, wherein the unilamellar liposome preparation is lyophilized prior to suspension in the external phase composition.

9. A method for preparing a cosmetic formulation, comprising:
 combining the liposomal suspension of claim 1 with a cosmetically suitable matrix to form a cosmetic formulation in the form of a cream, lotion, gel, serum, tonic, emulsion, paste, or spray.

10. A translucent unilamellar liposomal suspension comprising:
 a liposome preparation suspended in an external phase composition, the liposome preparation comprising a plurality of unilamellar liposomal particles having a unimodal size distribution and a mean particle size between about 50 nm to about 290 nm, the liposome preparation formed from an aqueous liposomal solution comprised of an oil-soluble composition and a water-soluble composition, the oil-soluble composition at a concentration between about 5% to about 33% by weight of the liposomal solution, the water-soluble composition at a concentration between about 67% to about 95% by weight of the liposomal solution,
 wherein the oil-soluble composition comprises a lecithin preparation, butylene glycol, ceramide IIIB, and β-sitosterol;

wherein the external phase composition comprises glycerin at a concentration between about 35% to about 75% by weight of the liposomal suspension; and wherein the liposomal suspension is translucent and has a refractive index between about 1.30 and about 1.45.

11. A stable unilamellar liposomal suspension comprising:

a liposome preparation suspended in an external phase composition, the liposome preparation comprising a plurality of unilamellar liposomal particles having a unimodal size distribution and a mean particle size between about 50 nm to about 290 nm, the liposome preparation formed from an aqueous liposomal solution comprised of an oil-soluble composition and a water-soluble composition, the oil-soluble composition at a concentration between about 5% to about 33% by weight of the liposomal solution, the water-soluble composition at a concentration between about 67% to about 95% by weight of the liposomal solution, wherein the oil-soluble composition comprises at least one phospholipid, at least one rigidity enhancer, and an antioxidant, and a coupling agent for solubilizing immiscible phases of differing polarity and having a dielectric constant of about 10.5 or greater at 23° C., wherein the antioxidant is selected from the group consisting of tocopherol, derivatives of tocopherol, alpha tocopherol, ascorbic acid, derivatives of ascorbic acid, butylated hydroxyl toluene, butylated hydroxyanisole, and mixtures thereof, wherein the at least one rigidity enhancer is selected from the group consisting of sphingolipid, phytosterol, cholesterol, and mixtures thereof and wherein the coupling agent is selected from the group consisting of butylene glycol, propylene glycol, hexylene glycol, and polyethylene glycol, and mixtures thereof;

wherein the external phase composition is at a concentration between about 30% to about 75% by weight of the liposomal suspension, the external phase composition comprising a viscosity promoting agent selected from thickening agents and having a density between about 0.95 g/cc and about 1.25 g/cc and a viscosity between about 2.5 cP and about 40,000 cP at a shear rate of 10 $sec^{-1}$ at 21° C.; and wherein the liposomal suspension is translucent to transparent, has a refractive index between about 1.30 and about 1.45, and retains its stability in neat form at a temperature of between about 4° C. to about 50° C. for a period of at least 30 days or at 21° C. for a period of at least 180 days.

12. The liposomal suspension of claim 11, wherein the coupling agent is butylene glycol.

13. The liposomal suspension of claim 11, wherein the at least one phospholipid comprises a glycerophospholipid with varying fatty acyl moieties or a sphingomyelin.

14. The liposomal suspension of claim 11, wherein the at least one phospholipid comprises a phospholipid preparation comprising phosphatidylcholine at a concentration of between about 80% to about 95% by weight of the phospholipid preparation.

15. The liposomal suspension of claim 11, comprising at least two rigidity enhancers, including at least one phytosterol and at least one member selected from the group consisting of ceramide, sphingosine, and phytosphingosine.

16. The liposomal suspension of claim 11, wherein the oil-soluble composition comprises butylene glycol, ceramide IIIB, β-sitosterol, and tocopherol.

17. The liposomal suspension of claim 11, wherein the liposomal suspension comprises glycerin at a concentration between about 35% to about 75% of the liposomal suspension.

* * * * *